United States Patent
Ben-Tsur et al.

(10) Patent No.: US 12,090,112 B2
(45) Date of Patent: Sep. 17, 2024

(54) METHODS AND SYSTEMS FOR ADAPTIVE TREATMENT OF DISORDERS IN THE GASTROINTESTINAL TRACT

(71) Applicant: VIBRANT LTD., Yokneam (IL)

(72) Inventors: Lior Ben-Tsur, Netanya (IL); Shai Molnar, Shorashim (IL); Roni Shabat, Kibbutz Yizra'el (IL); Shalom Lampert, Maalot (IL)

(73) Assignee: Vibrant Ltd., Yokneam (IL)

( * ) Notice: Subject to any disclaimer, the term of this patent is extended or adjusted under 35 U.S.C. 154(b) by 0 days.

(21) Appl. No.: 17/233,587

(22) Filed: Apr. 19, 2021

(65) Prior Publication Data

US 2021/0236381 A1 Aug. 5, 2021

Related U.S. Application Data

(63) Continuation of application No. 16/357,570, filed on Mar. 19, 2019, now Pat. No. 11,478,401, which is a (Continued)

(30) Foreign Application Priority Data

Sep. 21, 2016 (GB) ...................................... 1616044

(51) Int. Cl.
*A61H 23/02* (2006.01)
*A47L 17/00* (2006.01)
(Continued)

(52) U.S. Cl.
CPC .............. *A61H 23/02* (2013.01); *A47L 17/00* (2013.01); *A61B 5/073* (2013.01); *A61B 5/6861* (2013.01);
(Continued)

(58) Field of Classification Search
CPC ............ A61H 23/02; A61H 2201/1207; A61H 2201/5005; A61H 2205/083; A61B 5/073; A61B 5/6861; A61B 5/6871
See application file for complete search history.

(56) References Cited

U.S. PATENT DOCUMENTS 3,485,235 A 12/1969 Felson
4,239,040 A 12/1980 Hosoya et al.
(Continued)

FOREIGN PATENT DOCUMENTS

CN 1829466 A 9/2006
CN 101516314 A 8/2009
(Continued)

OTHER PUBLICATIONS

Smart capsule to target colon diseases', Ben Gruber, Sep. 30, 2015 https://www.reuters.com/article/us-smart-capsule-colon-idUSKCNORU1ZE20150930.
(Continued)

*Primary Examiner* — Tu A Vo
*Assistant Examiner* — Kelsey E Baller
(74) *Attorney, Agent, or Firm* — Momentum IP; Marc Van Dyke

(57) ABSTRACT

A system and a method for treatment of a disorder in a gastrointestinal tract of a subject, using a treatment protocol, the treatment protocol being based at least in part on data relating to other subjects and their responses to treatment with various treatment protocols.

21 Claims, 12 Drawing Sheets

Related U.S. Application Data continuation-in-part of application No. PCT/IB2017/055565, filed on Sep. 14, 2017.

(51) Int. Cl.
  *A61B 5/00* (2006.01)
  *A61B 5/07* (2006.01)
  *A61B 10/00* (2006.01)
  *E03D 9/00* (2006.01)

(52) U.S. Cl.
  CPC ........... *A61B 10/0038* (2013.01); *E03D 9/00* (2013.01); *A61H 2201/1207* (2013.01); *A61H 2201/5005* (2013.01); *A61H 2205/083* (2013.01)

(56) References Cited

U.S. PATENT DOCUMENTS

| | | | |
|---|---|---|---|
| 4,507,115 A | 3/1985 | Kambara et al. | |
| 5,170,801 A | 12/1992 | Casper et al. | |
| 5,991,931 A | 11/1999 | Hawkins et al. | |
| 6,453,199 B1 | 9/2002 | Kobozev | |
| 6,632,216 B2 | 10/2003 | Houzego et al. | |
| 6,776,165 B2 | 8/2004 | Jin | |
| 6,929,363 B2 | 8/2005 | Sakai et al. | |
| 6,984,205 B2 | 1/2006 | Gazdzinski | |
| 7,076,284 B2 | 7/2006 | Segawa et al. | |
| 7,354,397 B2* | 4/2008 | Fujita | A61B 1/00059 356/241.6 |
| 7,510,537 B2 | 3/2009 | Imboden et al. | |
| 7,797,033 B2 | 9/2010 | DAndrea et al. | |
| 7,942,811 B2 | 5/2011 | Segawa et al. | |
| 8,021,357 B2 | 9/2011 | Tanaka et al. | |
| 8,021,384 B2 | 9/2011 | Weiss et al. | |
| 8,036,748 B2* | 10/2011 | Zdeblick | A61M 31/002 607/30 |
| 8,038,600 B2 | 10/2011 | Uchiyama et al. | |
| 8,147,482 B2 | 4/2012 | Shimizu et al. | |
| 8,202,697 B2 | 6/2012 | Holmes | |
| 8,216,130 B2 | 7/2012 | Glukhovsky et al. | |
| 8,295,932 B2 | 10/2012 | Bitton et al. | |
| 8,306,592 B2 | 11/2012 | Takizawa et al. | |
| 8,518,022 B2 | 8/2013 | Trovato et al. | |
| 8,533,873 B2 | 9/2013 | West, Jr. | |
| 8,597,278 B2 | 12/2013 | Trovato et al. | |
| 8,701,677 B2 | 4/2014 | Duan et al. | |
| 8,755,888 B2 | 6/2014 | Voznesensky et al. | |
| 8,945,005 B2* | 2/2015 | Hafezi | A61B 5/1473 600/300 |
| 9,078,799 B2 | 7/2015 | Shohat et al. | |
| 9,156,169 B2 | 10/2015 | Duan et al. | |
| 9,232,909 B2 | 1/2016 | Duan et al. | |
| 9,511,211 B2 | 12/2016 | Tange et al. | |
| 9,532,923 B2 | 1/2017 | Shohat et al. | |
| 9,538,937 B2 | 1/2017 | Rohde et al. | |
| 9,572,746 B2 | 2/2017 | Asfora | |
| 9,707,150 B2 | 7/2017 | Shabbat | |
| 9,730,336 B2* | 8/2017 | Arneson | H05K 3/36 |
| 9,750,923 B2 | 9/2017 | Niichel et al. | |
| 9,770,588 B2 | 9/2017 | Bettinger | |
| 9,919,152 B2 | 3/2018 | Levine et al. | |
| 10,118,035 B2 | 11/2018 | Perez et al. | |
| 10,478,373 B2* | 11/2019 | Duan | A61H 23/0263 |
| 10,537,720 B2 | 1/2020 | Ben-Tsur | |
| 10,543,348 B2 | 1/2020 | Ben-Tsur | |
| 10,814,113 B2 | 10/2020 | Ben-Tsur | |
| 10,888,277 B1 | 1/2021 | Ben-Tsur | |
| 10,905,378 B1 | 2/2021 | Ben-Tsur | |
| 11,020,018 B2 | 6/2021 | Ben-Tsur | |
| 11,197,798 B2 | 12/2021 | Shohat et al. | |
| 2002/0099310 A1* | 7/2002 | Kimchy | A61B 6/425 600/587 |
| 2002/0132226 A1 | 9/2002 | Nair et al. | |
| 2003/0020810 A1 | 1/2003 | Takizawa et al. | |
| 2003/0191430 A1* | 10/2003 | D'Andrea | A61B 1/041 604/66 |
| 2004/0030454 A1 | 2/2004 | Kim et al. | |
| 2004/0175289 A1 | 9/2004 | Takizawa et al. | |
| 2004/0253304 A1 | 12/2004 | Gross et al. | |
| 2004/0267240 A1 | 12/2004 | Gross et al. | |
| 2005/0058701 A1 | 3/2005 | Gross et al. | |
| 2005/0085696 A1 | 4/2005 | Uchiyama et al. | |
| 2005/0148847 A1 | 7/2005 | Uchiyama et al. | |
| 2005/0177069 A1 | 8/2005 | Takizawa et al. | |
| 2006/0169293 A1 | 8/2006 | Yokoi et al. | |
| 2006/0211963 A1 | 9/2006 | Spirk et al. | |
| 2006/0270899 A1 | 11/2006 | Amirana | |
| 2006/0276729 A1 | 12/2006 | Reed et al. | |
| 2007/0015952 A1 | 1/2007 | Chang et al. | |
| 2007/0238940 A1 | 10/2007 | Amirana | |
| 2008/0161639 A1 | 7/2008 | Katayama et al. | |
| 2008/0188837 A1 | 8/2008 | Belsky et al. | |
| 2008/0269664 A1 | 10/2008 | Trovato et al. | |
| 2008/0275430 A1 | 11/2008 | Belsky et al. | |
| 2008/0281238 A1 | 11/2008 | Oohashi et al. | |
| 2009/0281380 A1 | 11/2009 | Miller et al. | |
| 2009/0306633 A1 | 12/2009 | Trovato et al. | |
| 2009/0318783 A1* | 12/2009 | Rohde | A61B 5/066 600/302 |
| 2009/0318841 A1 | 12/2009 | Shohat et al. | |
| 2010/0049012 A1 | 2/2010 | Dijksman et al. | |
| 2010/0217079 A1 | 8/2010 | Tichy | |
| 2010/0222670 A1 | 9/2010 | Demierre et al. | |
| 2011/0208011 A1 | 8/2011 | Ben-Horin | |
| 2011/0319727 A1 | 12/2011 | Ishihara | |
| 2012/0041778 A1 | 2/2012 | Kraft | |
| 2013/0158452 A1 | 6/2013 | Juto et al. | |
| 2013/0253387 A1 | 9/2013 | Bonutti et al. | |
| 2013/0267788 A1 | 10/2013 | Duan et al. | |
| 2014/0107726 A1* | 4/2014 | Voznesensky | A61N 1/37205 607/40 |
| 2014/0221741 A1* | 8/2014 | Wang | A61B 5/073 600/109 |
| 2015/0011829 A1 | 1/2015 | Wang et al. | |
| 2015/0018614 A1 | 1/2015 | Duan et al. | |
| 2015/0018615 A1 | 1/2015 | Duan et al. | |
| 2015/0045658 A1* | 2/2015 | Tange | A61M 37/00 600/424 |
| 2015/0065926 A1 | 3/2015 | Nakamura et al. | |
| 2015/0073315 A1 | 3/2015 | Shabbat | |
| 2015/0223727 A1 | 8/2015 | Kimchy et al. | |
| 2015/0380140 A1 | 12/2015 | Duan et al. | |
| 2016/0083405 A1* | 3/2016 | Lansalot-Matras | C23C 16/405 252/182.3 |
| 2016/0136104 A1* | 5/2016 | Niichel | A61B 5/0002 604/131 |
| 2016/0183878 A1 | 6/2016 | Weast et al. | |
| 2016/0287058 A1 | 10/2016 | Ye et al. | |
| 2016/0303133 A1 | 10/2016 | Dudley et al. | |
| 2016/0310357 A1 | 10/2016 | Duan et al. | |
| 2017/0020374 A1 | 1/2017 | Duan et al. | |
| 2017/0035407 A1 | 2/2017 | Duan et al. | |
| 2017/0035520 A1 | 2/2017 | Duan et al. | |
| 2017/0135897 A1 | 5/2017 | Shohat et al. | |
| 2017/0273863 A1 | 9/2017 | Shabbat | |
| 2017/0296425 A1 | 10/2017 | Duan et al. | |
| 2017/0296428 A1 | 10/2017 | Duan et al. | |
| 2017/0340242 A1 | 11/2017 | Duan | |
| 2018/0055597 A1 | 3/2018 | Puan et al. | |
| 2018/0084975 A1 | 3/2018 | Duan et al. | |
| 2018/0360355 A1* | 12/2018 | Chavan | A61B 5/6861 |
| 2019/0152663 A1 | 5/2019 | Kraft | |
| 2019/0224070 A1 | 7/2019 | Ben-Tsur | |
| 2020/0315541 A1* | 10/2020 | Ben-Tsur | A61B 5/0051 |
| 2020/0375438 A1* | 12/2020 | Laughlin | A61B 5/42 |
| 2021/0015428 A1* | 1/2021 | Yangdai | A61B 10/0045 |
| 2021/0268244 A1* | 9/2021 | Niichel | A61K 9/0053 |
| 2022/0218303 A1* | 7/2022 | Memon | A61B 8/4455 |

(56) References Cited

U.S. PATENT DOCUMENTS

| | | | | |
|---|---|---|---|---|
| 2022/0257195 | A1* | 8/2022 | Sladeczek | A61B 5/6861 |
| 2022/0409139 | A1* | 12/2022 | Ben-Tsur | A61B 5/073 |

FOREIGN PATENT DOCUMENTS

| | | | |
|---|---|---|---|
| CN | 101810481 | A | 8/2010 |
| CN | 102743174 | A | 10/2012 |
| CN | 102743175 | A | 10/2012 |
| CN | 102743176 | A | 10/2012 |
| CN | 202483565 | U | 10/2012 |
| CN | 102813515 | A | 12/2012 |
| CN | 102860810 | A | 1/2013 |
| CN | 202699138 | U | 1/2013 |
| CN | 202821355 | U | 3/2013 |
| CN | 202843564 | U | 4/2013 |
| CN | 202843608 | U | 4/2013 |
| CN | 202875332 | U | 4/2013 |
| CN | 103222842 | A | 7/2013 |
| CN | 203634116 | U | 6/2014 |
| CN | 104898850 | A | 9/2015 |
| CN | 105025245 | A | 11/2015 |
| CN | 105079970 | A | 11/2015 |
| CN | 105380777 | A | 3/2016 |
| CN | 105411505 | A | 3/2016 |
| CN | 205108749 | U | 3/2016 |
| CN | 205286889 | U | 6/2016 |
| CN | 105939451 | A | 9/2016 |
| CN | 105942959 | A | 9/2016 |
| CN | 105996961 | A | 10/2016 |
| CN | 106056588 | A | 10/2016 |
| CN | 106097335 | A | 11/2016 |
| CN | 106137760 | A | 11/2016 |
| CN | 106204599 | A | 12/2016 |
| CN | 205758500 | U | 12/2016 |
| CN | 106373137 | A | 2/2017 |
| CN | 205913317 | U | 2/2017 |
| CN | 205928774 | U | 2/2017 |
| CN | 106923787 | A | 7/2017 |
| CN | 106934799 | A | 7/2017 |
| CN | 107174188 | A | 9/2017 |
| CN | 107233580 | A | 10/2017 |
| CN | 107240091 | A | 10/2017 |
| CN | 107375951 | A | 11/2017 |
| EP | 2987447 | A1 | 2/2016 |
| EP | 2995240 | A1 | 3/2016 |
| JP | 2001062397 | A | 3/2001 |
| JP | 2002163359 | A | 6/2002 |
| JP | 2004081374 | A | 3/2004 |
| JP | 2005052502 | A | 3/2005 |
| JP | 2010503451 | A | 2/2010 |
| JP | 2010246703 | A | 11/2010 |
| JP | 2013535756 | A | 9/2013 |
| WO | 2006025013 | A1 | 3/2006 |
| WO | 2007013059 | A2 | 2/2007 |
| WO | 2008012700 | A1 | 1/2008 |
| WO | 2008035329 | A2 | 3/2008 |
| WO | 2009063375 | A1 | 5/2009 |
| WO | 2013121276 | A1 | 8/2013 |
| WO | 2018055487 | A1 | 3/2018 |

OTHER PUBLICATIONS

Advanced Delivery Devices—IntelliCap: An Intelligent, Electronic Capsule for Oral Drug Delivery & Development', Drug Development & Delivery, Apr. 2013 http://drug-dev.com/advanced-delivery-devices-intellicap-an-intelligent-electronic-capsule-for-oral-drug-delivery-development/.
Machine Translation (by Google Patents) for CN 102743174 published on Oct. 24, 2012.
Machine Translation (by Google Patents) for CN 102743175 published on Oct. 24, 2012.
Machine Translation (by Google Patents) for CN 102743176 published on Oct, 24, 2012.
Machine Translation (by Google Patents) for CN 102813515 published on Dec. 12, 2012.
Machine Translation (by Google Patents) for CN 102860810 published on Jan. 9, 2013.
Machine Translation (by Google Patents) for CN 03222842 published on Jul. 31, 2013.
Machine Translation (by Google Patents) for CN 104898850 published on Sep. 9, 2015.
Machine Translation (by Google Patents) for CN 105025245 published on Nov. 4, 2015.
Machine Translation (by Google Patents) for CN 105079970 published on Nov. 25, 2015.
Machine Translation (by Google Patents) for CN 105411505 published on Mar. 23, 2016.
Machine Translation (by Google Patents) for CN 105939451 published on Sep. 14, 2016.
Machine Translation (by Google Patents) for CN 105942959 published on Sep. 21, 2016.
Machine Translation (by Google Patents) for CN 105996961 published on Oct. 12, 2016.
Machine Translation (by Google Patents) for CN 106056588 published on Oct. 26, 2016.
Machine Translation (by Google Patents) for CN 106097335 published on Nov. 9, 2016.
Machine Translation (by Google Patents) for CN 106137760 published on Nov. 23, 2016.
Machine Translation (by Google Patents) for CN 106204599 published on Dec. 7, 2016.
Machine Translation (by Google Patents) for CN 106373137 published on Feb. 1, 2017.
Machine Translation (by Google Patents) for CN 106923787 published on Jul. 7, 2017.
Machine Translation (by Google Patents) for CN 106934799 published on Jul. 7, 2017.
Machine Translation (by Google Patents) for CN 107174188 published on Sep. 19, 2017.
Machine Translation (by Google Patents) for CN 107233580 published on Oct. 10, 2017.
Machine Translation (by Google Patents) for CN 107240091 published on Oct. 10, 2017.
Machine Translation (by Google Patents) for CN 107375951 published on Nov. 24, 2017.
Machine Translation (by Google Patents) for CN 1829466 published on Sep. 6, 2006.
Machine Translation (by Google Patents) for CN 202483565 published on Oct. 10, 2012.
Machine Translation (by Google Patents) for CN 202699138 published on Jan. 30, 2013.
Machine Translation (by Google Patents) for CN 202821355 published on Mar. 27, 2013.
Machine Translation (by Google Patents) for CN 202843564 published on Apr. 3, 2013.
Machine Translation (by Google Patents) for CN 202843608 published on Apr. 3, 2013.
Machine Translation (by Google Patents) for CN 202875332 published on Apr. 17, 2013.
Machine Translation (by Google Patents) for CN 203634116 published on Jun. 11, 2014.
Machine Translation (by Google Patents) for CN 205108749 published on Mar. 30, 2016.
Machine Translation (by Google Patents) for CN 205758500 published on Dec. 7, 2016.
Machine Translation (by Google Patents) for CN 205913317 published on Feb. 1, 2017.
Machine Translation (by Google Patents) for CN 205928774 published on Feb. 8, 2017.
Machine Translation (by Google Patents) for JP 2001062397 published on Mar. 13, 2001.
Machine Translation (by Google Patents) for JP 2010503451 published on Feb. 4, 2010.
Co-pending U.S. Appl. No. 15/882,283, filed Jan. 29, 2018.
Co-pending U.S. Appl. No. 15/882,289, filed Jan. 29, 2018.
Co-pending U.S. Appl. No. 16/747,635, filed Jan. 21, 2020.

(56) References Cited

OTHER PUBLICATIONS

Co-pending U.S. Appl. No. 16/403,553, filed May 25, 2019.
Co-pending U.S. Appl. No. 15/882,552, filed Jan. 29, 2018.
Co-pending U.S. Appl. No. 16/732,883, filed Jan. 2, 2020.
Co-pending U.S. Appl. No. 16/780,923, filed Feb. 4, 2020.
Co-pending U.S. Appl. No. 16/823,035, filed Mar. 18, 2020.
Co-pending U.S. Appl. No. 16/377,213, filed Apr. 7, 2019.
CN101810481 Machine Translation (by Google Patents)—published Aug. 25, 2010.
CN105380777 Machine Translation (by Google Patents)—published Oct. 27, 2017.
CN205286889 Machine Translation (by Google Patents)—published Jun. 8, 2016.
JP2002163359 Machine Translation (by Google Patents)—published Jun. 7, 2002.
JP2010246703 Machine Translation (by Google Patents)—published Nov. 4, 2010.
JP2005052502 Machine Translation (by Google Patents)—published Mar. 3, 2005.
JP2013535756 Machine Translation (by Google Patents)—published Sep. 12, 2013.
CN101516314 Machine Translation (by Google Patents)—published May 21, 2014.
JP2004081374 Machine Translation (by Google Patents)—published May 18, 2004.
Digestive Disease Week. "Vibrating capsule shows promising results in treating chronic constipation: Non-pharmacological therapy." ScienceDaily. ScienceDaily, May 3, 2014. <www.sciencedaily.com/releases/2014/05/140503141219.htm>.

* cited by examiner

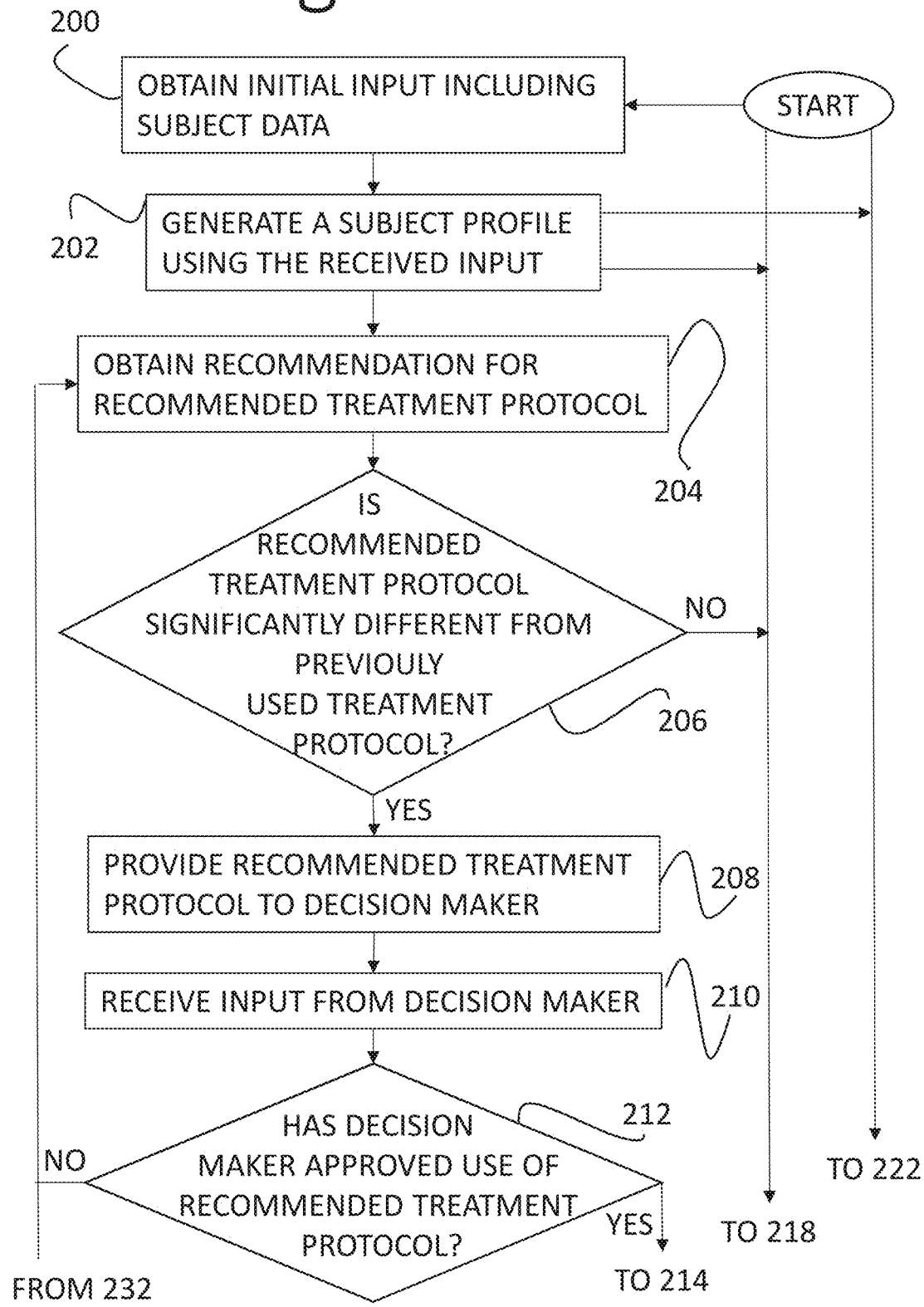

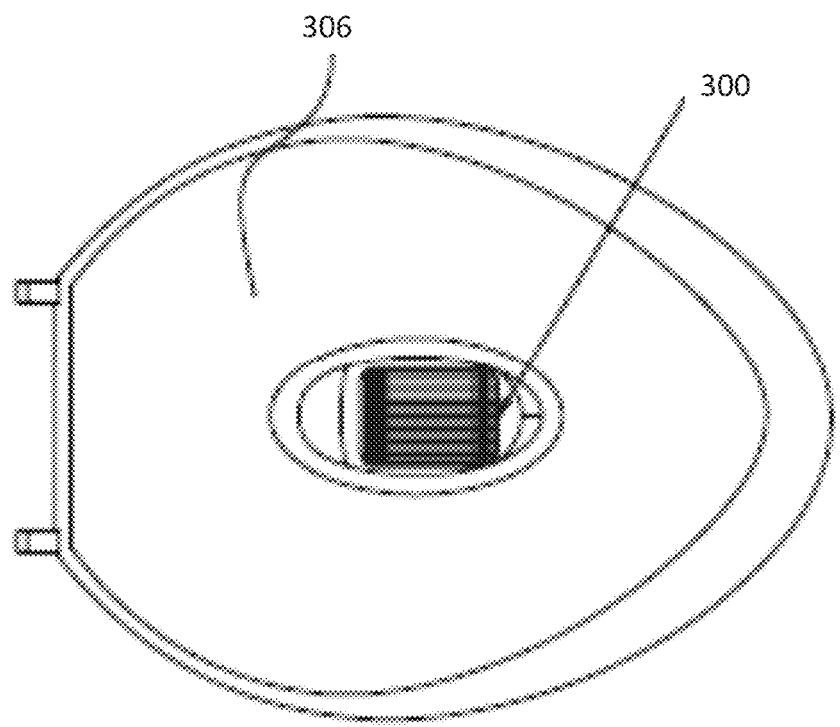

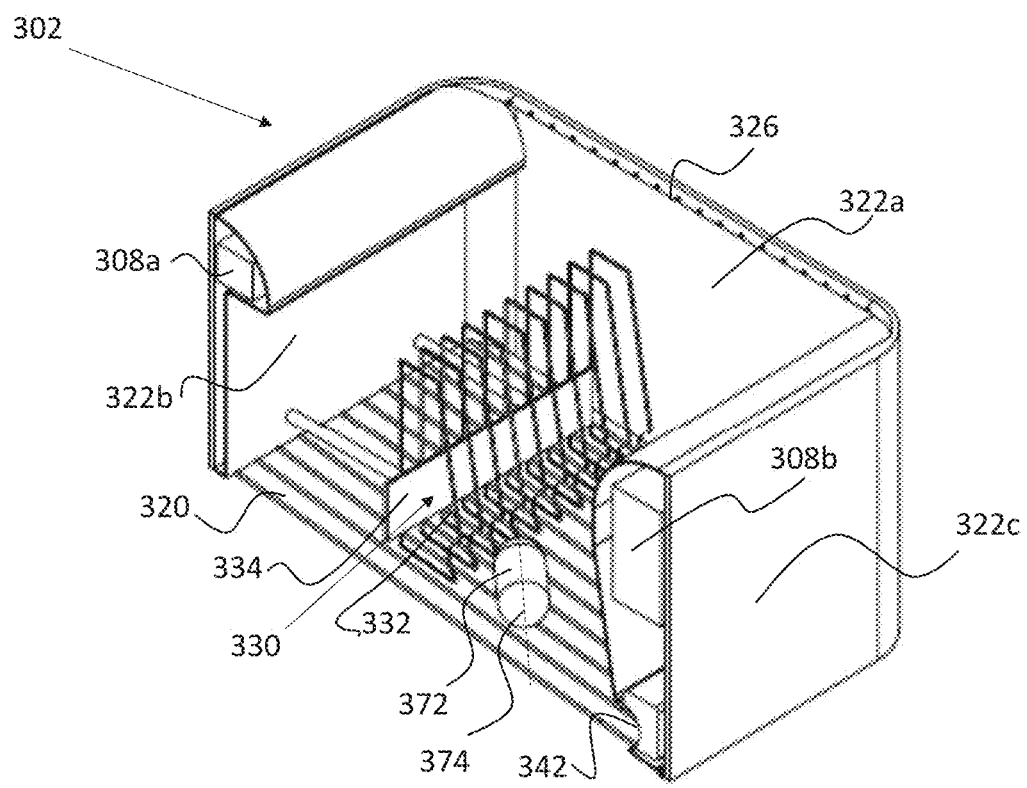

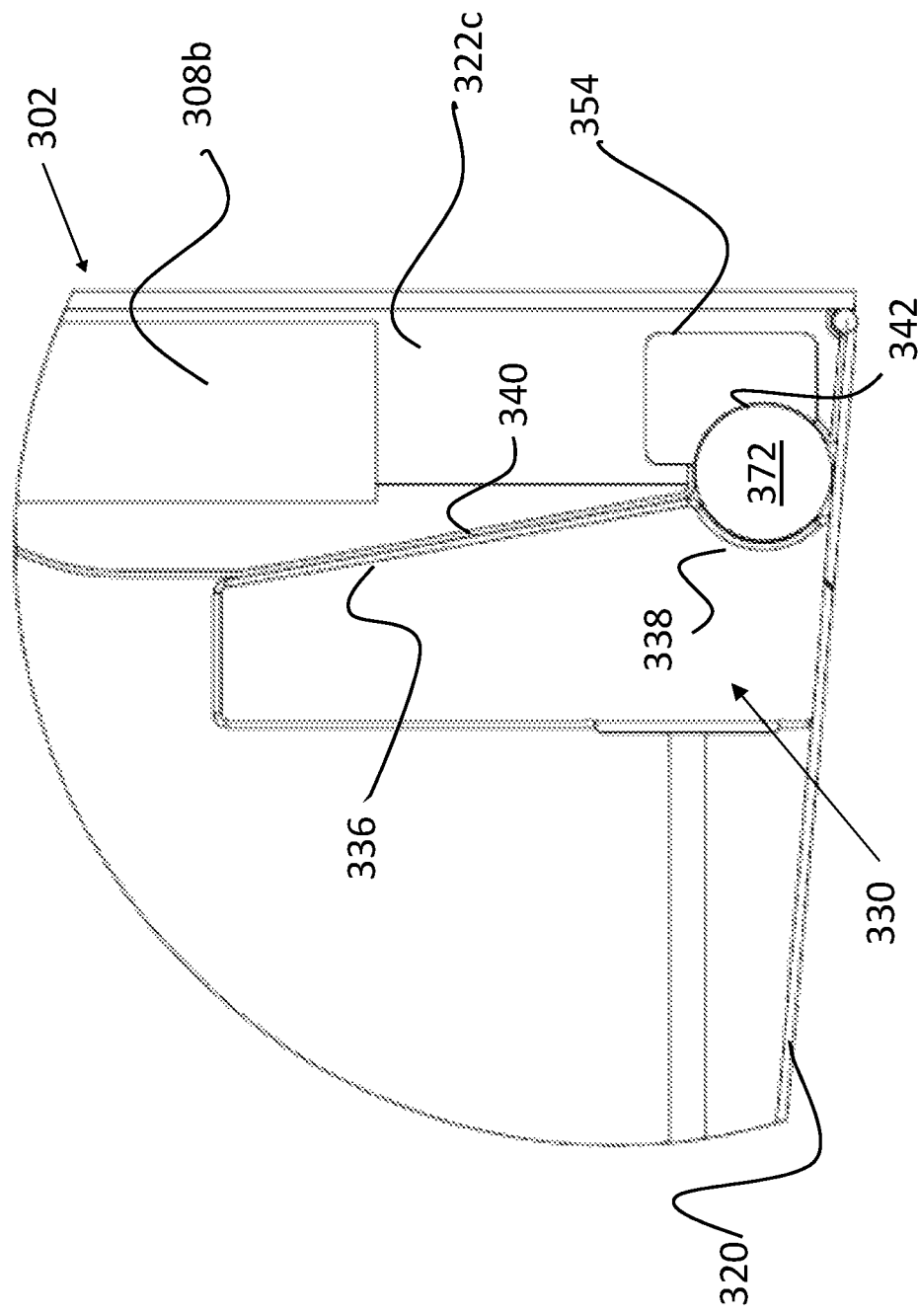

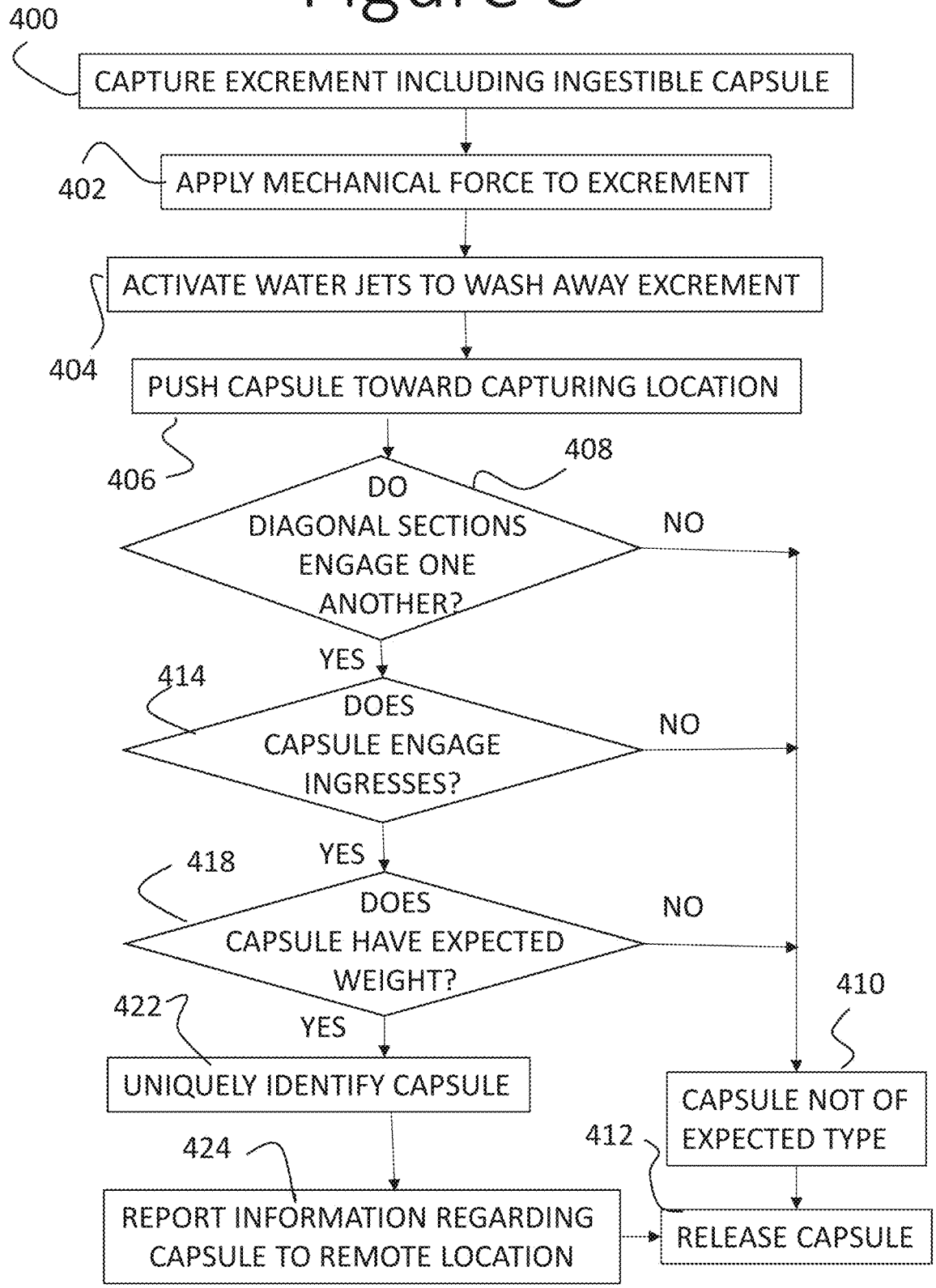

METHODS AND SYSTEMS FOR ADAPTIVE TREATMENT OF DISORDERS IN THE GASTROINTESTINAL TRACT

RELATED APPLICATIONS

The present application is a continuation in part of PCT Patent Application No. PCT/IB2017/055565, filed on Sep. 14, 2017, which gains priority from GB Patent Application No. 1616044.2, filed on Sep. 21, 2016, and from Chinese Patent Application No. 2017210463282, filed on Aug. 21, 2017, all of which are incorporated by reference as if fully set forth herein.

FIELD OF THE INVENTION

The present invention relates in general to medical devices and treatment systems, particularly to methods and systems for adapting a treatment protocol of ingestible capsules introducible to the gastrointestinal (GI) tract of a subject to the subject's response to one or more previous treatment protocols.

SUMMARY OF THE INVENTION

In accordance with an embodiments of the present invention, there is provided a method for treatment of a disorder in a gastrointestinal tract of a human subject, the method including:
(a) activating a first vibrating ingestible capsule to carry out a first vibration protocol defined in a first treatment protocol, the first vibration protocol including delivering vibrations to a wall of the GI tract of the subject, thereby to treat the subject;
(b) receiving feedback regarding a response of the subject to treatment in accordance with the first treatment protocol;
(c) based at least on the feedback, obtaining an updated recommendation for an updated recommended treatment protocol; and
(d) programming a second programmable vibrating ingestible capsule to implement a second vibration protocol defined in a second treatment protocol, the second treatment protocol being based on the updated recommended treatment protocol; and
(e) activating the second programmable vibrating ingestible capsule to carry out the second vibration protocol, the second vibration protocol including delivering vibrations to a wall of the GI tract of the subject, thereby to treat the subject,
wherein the updated recommendation is electronically obtained based on data included in a database, the data relating to at least one other subject.

In some embodiments, the first vibrating ingestible capsule includes a programmed capsule, programmed to implement the first vibration protocol.

In some embodiments, the first vibrating ingestible capsule includes a first programmable vibrating ingestible capsule.

In some embodiments, the method further includes, prior to (a):
(f) programming the first programmable vibrating , ingestible capsule to implement the first vibration protocol. In some embodiments, first vibration protocol includes a default vibration protocol. In some embodiments, the first treatment protocol includes a default treatment protocol.

In some embodiments, the method further includes, prior to (f):
(g) receiving from the subject initial input including subject data;
(h) obtaining an initial recommendation for an initial recommended treatment protocol based on at least one characteristic included in the subject data;
(i) generating the first treatment protocol based on the initial recommended treatment protocol,
wherein at least one of initial recommendation and the updated recommendation is electronically obtained based on data included in the database, the data relating to at least one other subject.

In some embodiments, the subject data includes at least one of demographic information, medical information, and treatment history of the subject.

In some embodiments, the data included in the database includes, for each of the at least one other subject, at least one of demographic information, medical information, and treatment history information. In some embodiments, the demographic information includes at least one of gender, age, date of birth, and geographical location. In some embodiments, the medical information includes at least one of information relating to disorders of the gastrointestinal tract, information relating to chronic diseases, and information relating to medicines taken regularly. In some embodiments, the treatment history includes at least one of information relating to treatment protocols used, and a response of the at least one other subject to treatment with the treatment protocols.

In some embodiments, obtaining the initial recommendation includes:
selecting the at least one characteristic of the subject from the received subject data;
identifying in the database a treatment protocol used for treatment of other subjects sharing the at least one characteristic with the subject; and
recommending the treatment protocol as the initial recommended treatment protocol.

In some embodiments, selecting the at least one characteristic includes selecting at least two characteristics of the subject, and wherein the identifying includes identifying in the database a treatment protocol used for treatment of other subjects sharing each of the at least two characteristics with the subject.

In some embodiments, identifying includes identifying in the database a treatment protocol successfully used fir treatment of the other subjects.

In some embodiments, the method further includes, following (h) and prior to (i):
providing the initial recommended treatment protocol to a decision maker; and
obtaining from the decision maker an indication whether or not the first treatment protocol should be identical to the initial recommended treatment protocol.

In some embodiments, the method further includes, if the indication obtained from the decision maker indicates that the first treatment protocol should not be identical to the initial recommended treatment protocol:
obtaining from the decision maker at least one change to be made to the initial recommended treatment protocol; and
applying the at least one change to the initial recommended treatment protocol thereby to obtain the first treatment protocol.

In some embodiments, the decision maker is a medical practitioner.

In some embodiments, the decision maker includes an electronic decision maker. In some embodiments, the at least one change obtained from the electronic decision maker is within predetermined limits for electronically changing the initial recommended treatment protocol. In some embodiments, the predetermined limits are defined in the subject data.

In some embodiments, programming the first programmable vibrating ingestible capsule includes:
providing the first vibration protocol to a capsule control unit, functionally associated with the first programmable vibrating ingestible capsule; and
the capsule control unit programming the first programmable vibrating ingestible capsule to implement the first vibration protocol.

In some embodiments, programming includes remotely transmitting the first vibration protocol to the first programmable vibrating ingestible capsule. In some embodiments, remotely transmitting includes transmitting the first vibration protocol using a short range wireless communication method. In some embodiments, remotely transmitting the first vibration protocol includes transmitting to the first programmable vibrating ingestible capsule a list of vibration parameters for effecting the first vibration protocol. In some embodiments, remotely transmitting the first vibration protocol includes transmitting to the first programmable vibrating ingestible capsule executable code for effecting the first vibration protocol.

In some embodiments, activating the first vibrating ingestible capsule includes activating a timer of the first vibrating ingestible capsule to immediately begin effecting the first vibration protocol. In some embodiments, activating the first vibrating ingestible capsule includes activating the first vibrating ingestible capsule to identify ingestion of the first vibrating ingestible capsule by the subject, and to begin effecting the first vibration protocol immediately following identification of ingestion of the first vibrating ingestible capsule.

In some embodiments, receiving feedback includes receiving from the subject feedback indicating times at which the subject experienced bowel movements during or following the treatment in accordance with the first treatment protocol. In some embodiments, receiving feedback includes receiving from the subject feedback indicating a physical feeling experienced by the subject during or following the treatment in accordance with the first treatment protocol. In some embodiments, receiving feedback includes receiving from the subject feedback indicating at least one characteristic of fecal matter excreted by the subject during or following the treatment in accordance with the first treatment protocol.

In some embodiments, receiving feedback includes receiving, from at least one sensor, information regarding expelling of the first vibrating ingestible capsule from the body of the subject. In some embodiments, the information regarding expelling includes a time at which the first vibrating ingestible capsule was expelled from the body of the subject. In some embodiments, the information regarding expelling includes an identification of the first vibrating ingestible capsule. In some embodiments, the identification includes at least one of an identification number, an MD, a barcode, and specific dimensions of the first vibrating ingestible capsule.

In some embodiments, receiving feedback further includes receiving from the at least one sensor information regarding at least one characteristic of fecal matter excreted from the body of the subject.

In some embodiments, the at least one sensor includes a toilet-bowl mounted sensor, and wherein the receiving the information from the sensor includes:
at the toilet-bowl mounted sensor, identifying at least one of the first vibrating ingestible capsule and fecal matter being expelled from the body of the subject;
at the toilet bowl sensor, gathering the information regarding expelling of the first vibrating ingestible capsule or of expelled fecal matter; and
transmitting the information from the toilet-bowl mounted sensor.

In some embodiments, receiving feedback includes receiving feedback from at least one of a medical practitioner or a care-giver of the subject regarding the response of the subject to treatment in accordance with the first treatment protocol.

In some embodiments, receiving feedback includes:
receiving from the subject feedback indicating at least one of times at which the subject experienced bowel movements and characteristics of fecal matter expelled during or following the treatment in accordance with the first treatment protocol; and
receiving, from at least one sensor, information indicating at least one of a time at which the first vibrating ingestible capsule was expelled from the body of the subject and characteristics of fecal matter expelled from the body of the subject; and
obtaining the updated recommendation includes:
comparing the feedback received from the subject to the information received from the at least one sensor;
assigning a reliability weight to the feedback received from the subject based on the comparison; and
taking the reliability weight of the feedback received by the user into consideration when using the feedback to obtain the updated recommendation.

In some embodiments, obtaining the updated recommendation includes:
selecting the at least one characteristic of the subject from at least one of the received subject data and the received feedback;
identifying in the database a treatment protocol used for treatment of other subjects sharing the at least one characteristic with the subject; and
recommending the treatment protocol as the updated recommended treatment protocol.

In some embodiments, selecting the at least one characteristic includes selecting from the received feedback at least one other characteristic relating to the response of the subject to the treatment with the first vibrating ingestible capsule, and wherein the identifying includes identifying in the database a treatment protocol used for treatment of other subjects who had a similar response to the treatment in accordance with the first treatment protocol.

In some embodiments, identifying includes identifying in the database a treatment protocol successfully used for treatment of the other subjects.

In some embodiments, the method further includes, following (c) and prior to (d):
providing the updated recommended treatment protocol to a decision maker; and
obtaining from the decision maker an indication whether or not the second treatment protocol should be identical to the updated recommended treatment protocol.

In some embodiments, the method further includes, if the indication obtained from the decision maker indicates that the second treatment protocol should not be identical to the updated recommended treatment protocol:

obtaining from the decision maker at least one change to be made to the updated recommended treatment protocol; and applying the at least one change to the updated recommended treatment protocol thereby to obtain the second treatment protocol.

In some embodiments, the decision maker is a medical practitioner. In some embodiments, the decision maker includes an electronic decision maker.

In some embodiments, programming the second programmable vibrating ingestible capsule includes:

providing the second vibration protocol to a capsule control unit, functionally associated with the second programmable vibrating ingestible capsule; and the capsule control unit programming the second programmable vibrating ingestible capsule to implement the second vibration protocol.

In some embodiments, programming the second programmable vibrating ingestible capsule includes remotely transmitting the second vibration protocol to the second programmable vibrating ingestible capsule. In some embodiments, remotely transmitting includes transmitting the second vibration protocol using a short range wireless communication method. In some embodiments, remotely transmitting the second vibration protocol includes transmitting to the second programmable vibrating ingestible capsule a list of vibration parameters for effecting the second vibration protocol. In some embodiments, remotely transmitting the second vibration protocol includes transmitting to the second programmable vibrating ingestible capsule executable code for effecting the second vibration protocol.

In some embodiments, activating the second programmable vibrating ingestible capsule includes activating a timer of the second programmable vibrating ingestible capsule to immediately begin effecting the second vibration protocol. In some embodiments, activating the second programmable vibrating ingestible capsule includes activating the second programmable vibrating ingestible capsule to identify ingestion of the second programmable vibrating ingestible capsule by the subject, and to begin effecting the second vibration protocol immediately following identification of ingestion of the second programmable vibrating ingestible capsule.

In some embodiments, the method further includes, following (c), using the received feedback together with subject data received from the subject to update the database to reflect the response of the subject to the treatment in accordance with the first treatment protocol.

In some embodiments, the method further includes, following (e), repeating steps (b)-(e).

In accordance with an embodiments of the present invention, there is provided a system for treatment of a disorder in a gastrointestinal tract of a human subject, the system including:

at least one input module adapted to receive input from a human, typically at least one of the subject, a medical practitioner treating the subject, and a care giver of the subject;

a computer readable memory adapted to store, or storing, a subject profile for the subject, the subject profile including subject data received as initial input by the at least one input module;

a database including data relating to subjects treated for disorders in the gastrointestinal tract and to treatment protocols used for the subjects;

a first vibrating ingestible capsule adapted to be activated to implement a first vibration protocol defined in a first treatment protocol, and adapted, in an operative mode, to deliver vibrations to a wall of the GI tract of the subject in accordance with the first vibration protocol, thereby to treat the subject;

a second programmable vibrating ingestible capsule adapted to be programmed and activated to implement a second vibration protocol defined in a second treatment protocol, and adapted, in an operative mode, to deliver vibrations to a wall of the GE tract of the subject in accordance with said second vibration protocol, thereby to treat the subject;

a processor, functionally associated with the at least one input module, the computer readable memory, and the database;

wherein the at least one input module is adapted to receive feedback regarding response of the subject to treatment in accordance with the first treatment protocol, wherein the processor is configured, based at least on the feedback, to:

automatically obtain an updated recommendation for an updated recommended treatment protocol based on at least one of said feedback, data included in said subject profile, and data included in said database, said data included in said database relating to at least one other subject of said subjects; and effect programming of the second programmable vibrating ingestible capsule to implement the second vibration protocol, the second treatment protocol including the second vibration protocol being based on the updated recommended treatment protocol.

In some embodiments, the first vibrating ingestible capsule includes a programmed capsule, programmed to implement the first vibration protocol.

In some embodiments, the first vibrating ingestible capsule includes a first programmable vibrating ingestible capsule.

In some embodiments, the processor is further configured to effect programming of the first programmable vibrating ingestible capsule to implement the first vibration protocol.

In some embodiments, the first vibration protocol includes a default vibration protocol. In some embodiments, the first treatment protocol includes a default treatment protocol.

In some embodiments, the processor is further configured, prior to effecting programming of the first programmable vibrating ingestible capsule, to:

obtain an initial recommendation for an initial recommended treatment protocol based on at least one characteristic included in the subject data; and generate the first treatment protocol based on the initial recommended treatment protocol, wherein the processor electronically obtains at least one of initial recommendation and the updated recommendation based on data included in the database, the data relating to at least one other subject of the subjects.

In some embodiments, the subject data includes at least one of demographic information, medical information, and treatment history information of the subject. In some embodiments, the data included in the database includes, for each of the at least one other subject, at least one of demographic information, medical information, and treatment history information. In some embodiments, the demographic information includes at least one of gender, age, date of birth, and geographical location, In some embodiments, the medical information includes at least one of information relating to disorders of the gastrointestinal tract, information relating to chronic diseases, and information relating to medicines taken regularly. In some embodiments, the treatment history information includes at least one of information relating to treatment protocols used, and a response of the at least one other subject to treatment with the treatment protocols.

In some embodiments, the processor is configured to obtain the initial recommendation by:

selecting the at least one characteristic of the subject from the subject data;

identifying in the database a treatment protocol used for treatment of other subjects sharing the at least one characteristic with the subject; and recommending the treatment protocol as the initial recommended treatment protocol.

In some embodiments, the processor is further configured to provide the initial recommended treatment protocol to a decision maker and to receive from the decision maker an indication whether or not the first treatment protocol should be identical to the initial recommended treatment protocol.

In some embodiments, the processor is further configured, if the indication received from the decision maker indicates that the first treatment protocol should not be identical to the initial recommended treatment protocol, to receive from the decision maker at least one change to be made to the initial recommended treatment protocol and to apply the at least one change to the initial recommended treatment protocol thereby to generate the first treatment protocol.

In some embodiments, the decision maker is a medical practitioner.

In some embodiments, the decision maker includes an electronic decision maker. In some embodiments, at least one change received from the electronic decision maker is within predetermined limits for electronically changing the initial recommended treatment protocol. In some embodiments, the predetermined limits are defined in the subject data.

In some embodiments, the system further includes a capsule control unit functionally associated with the processor and with the at least one second programmable vibrating ingestible capsule, the capsule control unit adapted to receive from the processor the second vibration protocol and to program the second programmable vibrating ingestible capsule to implement the second vibration protocol.

In some embodiments, the capsule control unit includes a communication module for remotely transmitting the second vibration protocol to the second programmable vibrating ingestible capsule. In some embodiments, the capsule control unit is adapted to remotely transmit the second vibration protocol using a short range wireless communication method. In some embodiments, the capsule control unit is adapted to remotely transmit to the second programmable vibrating ingestible capsule a list of vibration parameters for effecting the second vibration protocol. In some embodiments, the capsule control unit is adapted to remotely transmit to the second programmable vibrating ingestible capsule executable code for effecting the second vibration protocol.

In some embodiments, the first vibrating ingestible capsule includes a first programmable vibrating ingestible capsule, and wherein the capsule control unit is adapted to receive from the processor the first vibration protocol and to program the first programmable vibrating ingestible capsule to implement the first vibration protocol.

In some embodiments, the capsule control unit includes a communication module for remotely transmitting the first vibration protocol to the first programmable vibrating ingestible capsule. In some embodiments, the capsule control unit is adapted to remotely transmit the first vibration protocol using a short range wireless communication method. In some embodiments, the capsule control unit is adapted to remotely transmit to the first programmable vibrating ingestible capsule a list of vibration parameters for effecting the first vibration protocol. In some embodiments, the capsule control unit is adapted to remotely transmit to the first programmable vibrating ingestible capsule executable code for effecting the first vibration protocol.

In some embodiments, the feedback includes feedback received from the subject indicating times at which the subject experienced bowel movements during or following the treatment in accordance with the first treatment protocol. In some embodiments, the feedback includes feedback received from the subject indicating a physical feeling experienced by the subject during or following the treatment in accordance with the first treatment protocol. In some embodiments, the feedback includes feedback received from the subject indicating at least one characteristic of fecal matter excreted by the subject during or following the treatment in accordance with the first treatment protocol.

In some embodiments, the system further includes at least one sensor adapted to provide to the processor information regarding expelling of the first vibrating ingestible capsule from the body of the subject. In some embodiments, the information regarding expelling includes a time at which the first vibrating ingestible capsule was expelled from the body of the subject. In some embodiments, the information regarding expelling includes an identification of the first vibrating ingestible capsule. In some embodiments, the identification includes at least one of an identification number, an RFID, a barcode, and specific dimensions of the first vibrating ingestible capsule.

In some embodiments, the at least one sensor is further adapted to provide to the processor information. regarding at least one characteristic of excrement excreted from the body of the subject.

In some embodiments, the sensor provides the information to the processor as the feedback.

In some embodiments, the at least one sensor includes a toilet-bowl mounted sensor. In some embodiments, the toilet-bowl mounted sensor includes:

a receptacle adapted to be mounted within a toilet bowl and to receive excrement therein, the receptacle including:
  a first side wall, a second side wall, a third side wall, and a fourth side walls, the first and fourth side walls being generally opposite one another, the second and third side walls being generally opposite one another, and the third side wall including a side wall ingress; and
  a floor surface attached to the first, second, third, and fourth side walls, the floor surface including a wire frame or a mesh including openings suitable for removal of excrement from the receptacle;

a pushing mechanism, movable relative to the receptacle and adapted to push content of the receptacle, the pushing mechanism including a movable ingress;

a capsule measuring and/or identification mechanism, adapted to at least one of measure dimensions of an ingestible capsule included in the excrement and uniquely identify the ingestible capsule;

a capsule releasing mechanism for releasing the ingestible capsule from the receptacle; and a controller for controlling operation of the pushing mechanism, the capsule releasing mechanism, and the capsule measuring and: or identification mechanism, wherein the capsule measuring and/or identification mechanism includes a hollow formed between the side wall ingress and the movable ingress when the pushing mechanism is adjacent the third side wall, the hollow being suitable for enclosing the capsule.

In some embodiments, motion of the pushing mechanism is adapted to apply force to the excrement in the receptacle thereby to break-down the excrement to be suitably sized for removal via the openings. In some embodiments, the pushing mechanism is adapted to sense at least one characteristic of the excrement based on an amount of the force applied to the excrement in order to break down the excrement.

In some embodiments, the hollow formed between the movable ingress and the side wall ingress has a predetermined cross section, the predetermined cross section being suitably sized to match at least one of a cross section and a diameter of a specific type of capsule expected to be expelled into the receptacle.

In some embodiments, the capsule measuring and/or identification mechanism includes at least one first sensor mounted on the third side wall and adapted to sense engagement between a surface of the pushing mechanism and the third side wall.

In some embodiments, the capsule measuring and/or identification mechanism includes at least one second sensor mounted onto the side wall ingress, and adapted to sense engagement between an exterior surface of a capsule and a surface of the side wall ingress.

In some embodiments, the capsule measuring and/or identification mechanism includes a weighing mechanism adapted to sense a weight of a capsule captured in the hollow.

In some embodiments, the capsule measuring and/or identification mechanism further includes a capsule identification system, adapted to uniquely identify a capsule captured in the hollow.

In some embodiments, the controller is adapted to receive input from the capsule measuring and/or identification mechanism relating to the ingestible capsule following capturing thereof in the hollow, and to provide information based on the input to the processor. In some embodiments, the controller is adapted to receive input from the pushing mechanism relating to at least one characteristic of the excrement, and to provide information based on the input to the processor.

In some embodiments, the feedback includes feedback received from at least one of a medical practitioner or a care-giver of the subject regarding the response of the subject to the treatment in accordance with the first treatment protocol.

In some embodiments, the processor is further configured to use the subject data and the received feedback to update the database to reflect the response of the subject to the treatment in accordance with the first treatment protocol.

In accordance with an embodiments of the present invention, there is provided a toilet-bowl mounted sensor, including:
 a receptacle adapted to be mounted within a toilet bowl and to receive excrement therein, the receptacle including:
  a first side wall, a second side wall, a third side wall, and a fourth side walls, the first and fourth side walls being generally opposite one another, the second and third side walls being generally opposite one another, and the third side wall including a side wall ingress; and
  a floor surface attached to the first, second, third, and fourth side walls, the floor surface including a wire frame or a mesh including openings suitable for removal of excrement from the receptacle;
 a pushing mechanism, movable relative to the receptacle and adapted to push content of the receptacle, the pushing mechanism including a movable ingress;
 a capsule measuring and/or identification mechanism, adapted to at least one of measure dimensions of an ingestible capsule included in the excrement and uniquely identify the ingestible capsule;
 a capsule releasing mechanism for releasing the ingestible capsule from the receptacle; and
 a controller for controlling operation of the pushing mechanism, the capsule releasing mechanism, and the capsule measuring and/or identification mechanism,
 wherein the capsule measuring and/or identification mechanism includes a hollow formed between the side wall ingress and the movable ingress when the pushing mechanism is adjacent the third side wall, the hollow being suitable for enclosing the ingestible capsule.

In some embodiments, the sensor further includes a seal circumferentially arranged about the receptacle, wherein the receptacle and the seal are sized to circumferentially engage and seal against the toilet bowl along an entire cross section thereof, such that all matter expelled into the toilet bowl is received in the receptacle.

In some embodiments, at least one of the first, second, third, and fourth side walls includes a plurality of water jets, functionally associated with a conduit, the water jets adapted to receive water from the conduit and to spray the water into the receptacle for washing out excrement therefrom.

In some embodiments, the openings in the floor surface are suitably sized so that the ingestible capsule cannot pass through the openings.

In some embodiments, the floor surface is angled from the second side wall toward the third side wall, such that gravity assists in directing the ingestible capsule toward the capsule measuring and/or identification mechanism.

In some embodiments, the pushing mechanism extends generally parallel to the second side wall, and is movable between the second and third side walls. In some embodiments, motion of the pushing mechanism is adapted to apply force to the excrement in the receptacle thereby to break-down the excrement to be suitably sized for removal via the openings.

In some embodiments, during the motion, the pushing mechanism is adapted to sense at least one characteristic of the excrement based on and amount of the force applied to the excrement in order to break down the excrement.

In some embodiments, the pushing mechanism includes a plurality of wire frame elements connected to one another by a connector surface.

In some embodiments, the hollow formed between the movable ingress and the side wall ingress has a hollow cross section, the cross section being suitably sized to match at least one of a cross section and a diameter of a specific type of ingestible capsule expected to be expelled into the receptacle.

In some embodiments, the capsule measuring and/or identification mechanism includes at least one first sensor mounted on the third side wall and adapted to sense engagement between a surface of the pushing mechanism and the third side wall. In some embodiments, the capsule measuring and/or identification mechanism further includes at least one second sensor mounted onto the side wall ingress, and adapted to sense engagement between an exterior surface of an ingestible capsule captured in the hollow and a surface of the side wall ingress.

In some embodiments, the capsule measuring and/or identification mechanism including a weighing mechanism adapted to sense a weight of an ingestible capsule captured in the hollow. In some embodiments, the weighing mechanism forms part of, or is mounted on, the capsule releasing mechanism.

In some embodiments, the capsule measuring and/or identification mechanism includes a capsule identification system, adapted to uniquely identify an ingestible capsule captured in the hollow. In some embodiments, the capsule identification system includes a barcode reader adapted to read a barcode printed on an exterior surface of the ingestible capsule captured in the hollow, thereby to uniquely identify the ingestible capsule. In some embodiments, the capsule identification system includes a QR-code reader adapted to read a QR-code printed on an exterior surface of the ingestible capsule captured in the hollow, thereby to uniquely identify the ingestible capsule. In some embodiments, the capsule identification system includes a text interpretation mechanism adapted to capture and interpret an identification number or text printed on an exterior surface of the ingestible capsule captured in the hollow, thereby to uniquely identify the ingestible capsule. In some embodiments, the capsule identification system includes an image processing mechanism adapted to capture and interpret an image printed on an exterior surface of the ingestible capsule captured in the hollow, thereby to uniquely identify the ingestible capsule. In some embodiments, the capsule identification system includes an RFID tag reader adapted to read an RFID tag mounted onto the ingestible capsule captured in the hollow, thereby to uniquely identify the ingestible capsule.

In some embodiments, the capsule releasing mechanism includes a hinged portal formed in the floor surface beneath the side wall ingress, such that opening of the portal releases the ingestible capsule from the hollow and from the receptacle. In some embodiments, opening and closing of the portal is controlled by the controller.

In some embodiments, the controller is adapted to receive input from the capsule measuring and/or identification mechanism relating to the ingestible capsule following capturing thereof, and to provide capsule information based on the input to a remote location. In some embodiments, the controller is adapted to receive input from the pushing mechanism relating to at least one characteristic of the excrement, and to provide excrement information based on the input to a remote location.

In some embodiments, the controller is adapted to provide at least one of the capsule information and the excrement information by wired communication with the remote location, via a communication wire extending from the controller along the toilet bowl. In some embodiments, the controller is adapted to provide at least one of the capsule information and the excrement information by wireless communication with the remote location.

In some embodiments, the capsule information provided to the remote location includes at least one of a time at which the ingestible capsule was expelled into the receptacle or captured in the hollow, dimensions of the ingestible capsule, a weight of the ingestible capsule, and an identification of the ingestible capsule.

In some embodiments, the controller is adapted to provide power to the pushing mechanism, the capsule measuring and/or identification mechanism, and the capsule releasing mechanism. In some embodiments, the controller is adapted to receive power from a power supply wire extending along the toilet bowl.

In accordance with an embodiments of the present invention, there is provided a method for measuring and identifying an ingestible capsule expelled into a toilet bowl, the method including:

mounting a sensor as described herein in the toilet bowl, such that matter expelled into the toilet bowl, including the ingestible capsule, is received in the receptacle;

breaking down excrement included in the matter so that excrement is sized to be removed from the receptacle via the openings in the floor surface;

pushing the ingestible capsule toward the third side wall thereby capturing the ingestible capsule in the hollow; and measuring whether at least one of a cross section of the ingestible capsule matches an expected cross section and a diameter of the ingestible capsule matches an expected diameter.

In some embodiments, breaking down includes moving the pushing mechanism back and forth between the second and third side walls, thereby to break down the excrement.

In some embodiments, measuring includes weighing the ingestible capsule. In some embodiments, the method further includes, following the capturing, uniquely identifying the capsule.

In some embodiments, the method further includes reporting at least one of measurements of the ingestible capsule, a weight of the ingestible capsule, and an identity of the ingestible capsule to a remote location.

In some embodiments, reporting is only carried out if the cross section of the ingestible capsule matches the expected cross section or if the diameter of the ingestible capsule matches the expected diameter. In some embodiments, reporting is only carried out if a weight of the ingestible capsule matches an expected weight.

In some embodiments, the method further includes, following the measuring, releasing the ingestible capsule from the receptacle via the capsule releasing mechanism.

BRIEF DESCRIPTION OF THE FIGURES

The foregoing discussion will be understood more readily from the following detailed description of the invention, when taken in conjunction with the accompanying FIGS. 1, 2A-2B, 3A-3C, 4, 5A-5B, and 6-8, in which:

FIGS. 2A and 2B together are a schematic flowchart of a method for treatment of a disorder in the gastrointestinal tract of a subject according to the present invention, the method utilizing the inventive system of FIG. 1;

FIGS. 3A, 3B, and 3C are, respectively, a partially cut away side plan view, a partially cut away perspective view, and a top plan view of an inventive toilet-bowl mounted sensor for capturing and identifying an ingestible capsule according to the present invention, the toilet-bowl mounted sensor forming part of the system of FIG. 1;

FIGS. 5A and 5B are, respectively, a perspective view and a sectional view of the receptacle of FIG. 4 in an operational mode;

FIG. 6 is a partial sectional view of the receptacle of FIG. 4 in a capsule capturing mode;

FIG. 8 is a schematic flowchart of a method for capturing and identifying an ingestible capsule that has been expelled into a toilet bowl according to the present invention, the method utilizing the inventive toilet-bowl mounted sensor of any one of FIGS. 3A-7.

DESCRIPTION OF THE PREFERRED EMBODIMENTS

Figure 1:
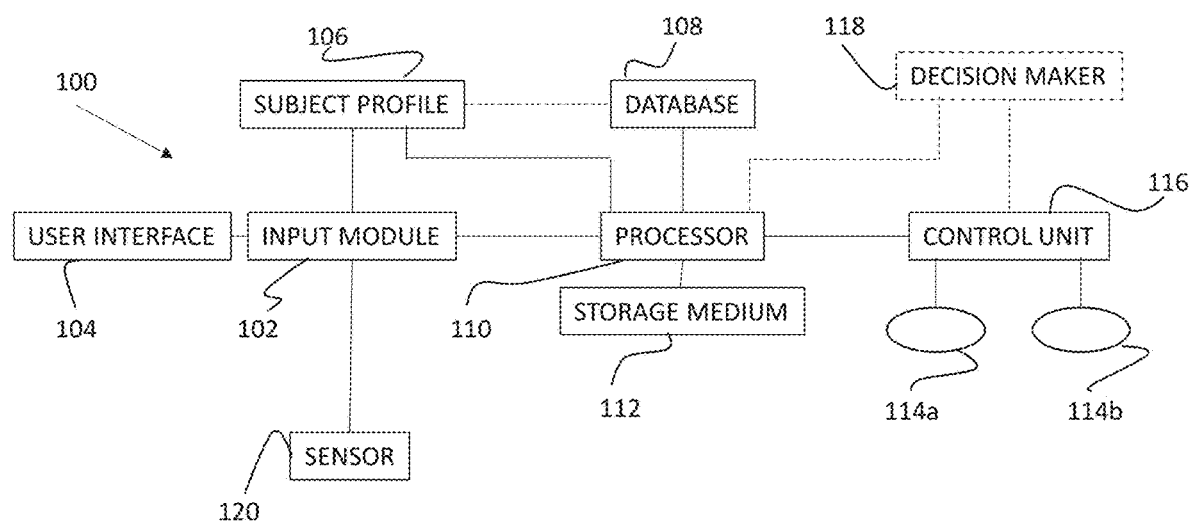
FIG. 1 is a schematic block diagram of a system for treatment of a disorder in the gastrointestinal tract of a subject according to an embodiment of the present invention.

The principles of the inventive system and method for treatment of a disorder in the gastrointestinal tract of a subject, and the inventive toilet-bowl mounted sensor for capturing and identifying an ingestible capsule that has been expelled into a toilet-bowl and method of use thereof, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this application, the term "subject" relates to a human subject.

For the purposes of this application, the term "vibrating ingestible capsule" relates to an ingestible capsule adapted to at least intermittently vibrate, for a cumulative duration of at least one minute, in accordance with a vibration protocol of the capsule, such that, when the capsule is disposed in the gastrointestinal (GI) tract of a subject and is in operative mode, the vibrations are delivered to a wall of the GI tract of the subject, so as to provide mechanical stimulation to the GI tract of the subject. Typically, such mechanical stimulation is provided so as to treat GI disorders such as constipation, diarrhea, gastroparesis, obesity, and the like.

For the purposes of this application, the term "programmable vibrating ingestible capsule" relates to a vibrating ingestible capsule adapted to vibrate in accordance with vibration protocol, the vibration protocol adapted to be programmed into the capsule by a capsule control unit. Specifically, the vibration protocol of a programmable vibrating ingestible capsule may be changed by re-programming the capsule to implement a different vibration protocol.

For the purposes of this application, the term "programmed vibrating ingestible capsule" relates to a vibrating ingestible capsule adapted to vibrate in accordance with a vibration protocol, the vibration protocol being programmed into the capsule, for example by the manufacturer thereof. The programmed vibration protocol is fixed, and the capsule cannot be re-programmed For the purposes of this application, the term "capsule control unit" relates to a device adapted to produce a vibrating ingestible capsule and/or to activate a vibrating ingestible capsule. Typically, the capsule control limit is adapted to receive a vibration protocol, and to transmit the vibration protocol to a vibrating ingestible capsule, thereby to program the capsule to implement the vibration protocol. For example, the capsule control unit may provide the vibration protocol to a processor of the programmable vibrating ingestible capsule by means of remote communication, such as by short range wireless communication, and may provide the protocol as a list of parameters, as executable code, or in any other manner suitable for the capsule to implement the vibration protocol. For activation, the capsule control unit typically is adapted to transmit an activation signal to a vibrating ingestible capsule, indicating to a processor of the capsule that the vibration protocol should be initiated. In some cases, the capsule control unit is also adapted to receive a signal from the capsule, indicating that the programmed vibration protocol and/or the activation instruction have been received.

For the purposes of this application, the term "short range wireless communication method" relates to any wireless communication method or protocol in which signals are communicated up to a maximum range of at most 1 kilometer, at most 500 meters, at most 300 meters, at most 200 meters, at most 100 meters, at most 50 meters, or at most 10 meters such as, for example, Bluetooth communication, Wi-Fi communication, RFID signal communication, low frequency magnetic field, and the like.

For the purposes of this application, the term "intermittently activated vibration engine" refers to a vibration engine which is adapted to vibrate at certain times and not to vibrate at other times, the activation times being selected by a processor or other control unit controlling the vibration engine, such as a processor of a vibrating ingestible capsule of which the vibration engine forms part.

For the purposes of this application, the term "vibration protocol" relates to a protocol specifying vibration parameters of an intermittently activated vibration engine of a vibrating ingestible capsule. Typically, the vibration protocol relates to a vibration rate (number of vibration cycles per hour) which is typically in the range of 1-300 cycles per hour, a vibration period and a repose period for each vibration cycle, a vibration frequency which is typically in the range of 1-500 Hz, an amount of force to be exerted by the vibrations, a set of vibration and non-vibration durations (i.e. a set specifying that the capsule vibrates at the vibration rate for a certain duration or a certain number of cycles, then rests for a certain duration, vibrates again for a certain duration or number of cycles, and so forth), and the like. In some cases, the vibration protocol may also relate to an activation delay for initiating vibration (a duration between activation of the capsule and the first activation of the vibration engine) which is typically in the range of 0-24 hours. The vibration and non-vibration durations may be defined as absolute times, or may be relative to ingestion or activation of the capsule. For example, a treatment protocol may indicate that the activation delay is 4 hours (i.e. intermittently activated vibration engine should begin vibration 4 hours after activation or ingestion of the capsule), and that following the activation delay the capsule should vibrate at a frequency of 150 Hz and at a duty cycle of 60%, for a duration of 2 hours, stop vibrating for 2 hours, and subsequently resume vibration for a duration of four hours, at a frequency of 250 Hz and at a duty cycle of 85%, each cycle having a vibration period of 3 seconds and a repose period of 26 seconds. As another example, the activation delay is 8 hours, and subsequently vibration begins at 200 Hz at a 40% duty cycle in repetitive cycles having a 1 second vibration period followed by a 27 second repose period. After each five cycles of vibration, the vibration frequency is increased by 2 Hz, and the duty cycle is increased by 1%.

For the purposes of this application, the term "treatment procedure" relates to parameters of a treatment using vibrating ingestible capsules, which are typically defined by a treating physician or medical practitioner. For example, the treatment procedure may include the number of capsule to be taken in a specific time duration (e.g. 3 capsules per week, 2 capsules per day, etc.), the frequency at which capsules should be taken, the time of day at which capsules should be taken, whether the capsule should be taken with or without food, and the like.

For the purpose of this application, the term "treatment protocol" relates to all aspects of treatment of a subject with a vibrating ingestible capsule, and includes the treatment procedure as well as the vibration protocol to be used for treating the subject.

For the purposes of this application, the term "default treatment protocol" relates to a standard treatment protocol which is typically used when initially treating a subject with a vibrating ingestible capsule, or when insufficient information is available for tailoring a specific treatment protocol to the subject.

For the purposes of this application, the terms "default vibration protocol" relates to a standard vibration protocol which is typically used when initially treating a subject with a vibrating ingestible capsule, or when insufficient information is available for tailoring a specific vibration protocol to the subject. In some cases, the default vibration protocol is the vibration protocol used by programmed vibrating ingestible capsules.

For the purposes of this application, the term "electronically obtained", when relating to a treatment protocol, relates to a treatment protocol which was generated by or determined by a machine based on electronic information, such as information included in a computerized or electronic profile of a subject and/or data included in a database, without direct human input or intervention.

For the purposes of this application, the term "successful treatment", and variations thereof, relates to treatment of a subject with one or more capsules implementing a specific treatment protocol such that during or following the treatment, the symptoms of the subject are improved by a significant degree, as defined by medical practices. For treatment of chronic constipation, successful treatment is treatment that results in an increase of at least one bowel movement per two-weeks, an increase of at least one bowel movement per week, an increase of three bowel movements per two-weeks, or an increase of at least two bowel movements per week, on average.

For the purposes of this application, the term "decision maker" relates to any entity capable of applying logic to a proposed treatment protocol, in order to determine whether or not the proposed treatment protocol is suitable for treatment of a subject, and/or whether the proposed treatment protocol must be modified in order to be suitable for treatment of the subject. The decision maker may be a human, or a machine including suitable artificial intelligence or logic components.

For the purposes of this application, the term "electronic decision maker" relates to a decision maker which is fully based on artificial intelligence or logic, and which makes decisions regarding the suitability of a proposed treatment protocol for treatment of a subject without direct input from a human, only based on artificial logic and/or intelligence. The electronic decision maker is typically limited to decisions within a scope determined by a human, such as a medical practitioner, prior to use of the electronic decision maker. For example, a doctor may define a range of vibration protocols which is acceptable for use for a subject, and the electronic decision maker may make decisions within that range, but would refer to a human decision maker if decisions are required that are outside of the predefined range.

Referring now to the drawings, FIG. 1 is a schematic block diagram of a system 100 for treatment of a disorder in the gastrointestinal tract of a subject according to an embodiment of the present invention.

As seen in FIG. 1, system 100 includes at least one input module 102 operative to receive input from at least one of the subject, a medical practitioner or medical personnel treating the subject, and a care giver of the subject, such as a parent, guardian, or personal medical aide, for example via a user interface 104. The input module 102 may further be operative to receive input from one or more sensors, as described in further detail hereinbelow. In some embodiments, separate input modules 102 and/or different user interfaces 104 are used for different input providers.

The input module 102 may be any suitable input module, and may include, for example, a receiver or transceiver configured to receive the input as a communication signal from a remote location, such as from the one or more sensors, or a keyboard or touchpad configured to receive input entered directly thereinto, for example by the subject, a caretaker of the subject, medical personnel treating the subject, or any other input provider.

A computer readable memory stores a subject profile 106 for the subject, including subject data. The subject profile 106 may be functionally associated with the input module 102, and the subject data may be provided to the subject profile 106 as input, via one of more input module 102. For example, the subject, the medical practitioner or medical personnel treating the subject, or the care giver of the subject may provide the subject data, for example as an initial input.

In some embodiments, the subject data includes demographic information of the subject, such as the subject's name, identification number such as a social security number or passport number, address, date of birth, age, gender, contact information, and emergency contact information.

In some embodiments, the subject data includes medical information of the subject, such as the subject's medical history and particularly the medical history of constipation, diarrhea, gastroparesis, obesity, and/or gastrointestinal diseases, medications and/or treatments previously tried by the subject, particularly for constipation, diarrhea, gastroparesis, obesity, and/or gastrointestinal diseases, results of medical examination such as etiology of constipation, results from physical examination such as digital rectal examinations, results from gastrointestinal explorations such as transit or motility studies, anorectal manometry, balloon test expulsion, scintigraphy scan, or other gastrointestinal explorations, blood test information, stool sample information, microbiome information, information relating to allergies, chronic diseases, medications currently being used, and the like. In some embodiments, the medical information may be collected before, during, and/or after treatment in accordance with the method described herein.

In some embodiments, the subject data may also include information relating to the subject's lifestyle, such as diet, water intake, and physical activity.

In some embodiments, for female subjects, the subject data may also include obstetric medical history.

In some embodiments, the subject data may include guidelines for treatment of the subject, or a "treatment safe zone" or "self adapting zone" for the subject, such as, for example, a range of vibration protocols suitable for safe treatment of the subject, which may be used by an electronic decision maker as described in further detail hereinbelow.

In some embodiments, the system includes a database 108, which may be functionally associated with one or more input module 102 and/ or with subject profile 106. Database 108 includes data relating to subjects treated tier disorders in the gastrointestinal tract. In some embodiments, data is input into the database 108 directly by an input provider, such as one or more subjects, a medical practitioner, medical personnel, a researcher or administrator at a research facility, and the like, for example via input module 102 and user interface 104. In some embodiments, the data is input into the database 108 automatically, for example directly from the subject profile 106, as described in further detail hereinbelow.

In some embodiments, data included in database 108 relates to at least one other subject, and preferably to a plurality of subjects other than the subject.

In some embodiments, the data included in database 108 includes, for each other subject, demographic information such as gender, age, date of birth, and the like, as well as information relating to disorders of the gastrointestinal tract experienced by the other subject, to treatments provided for such disorders, and to the other subject's response to such treatments. In some embodiments, the data included in database 108 may be substantially parallel to the subject data. Specifically, in some embodiments, the data included in the database lists, for each of the other subjects, one or more vibration protocols, treatment procedures, and/or treatment protocols used to treat the other subject, and the other subject's response to treatment with such protocols and procedures.

A processor 110 is functionally associated with subject profile 106 and with database 108, and may further be functionally associated with input module 102. Processor 110 is functionally associated with a computer readable storage medium 112 storing instructions, which may be carried out by the processor 110, as explained in further detail hereinbelow with respect to FIGS. 2A and 2B.

In some embodiments, processor 110 is configured to receive, for example via input module 102 or via subject profile 106, feedback relating to a response of the subject to treatment with a specific treatment protocol, a specific vibration protocol, or specific treatment procedures. For example, the feedback may indicate times at which the subject experienced bowel movements following the treatment, a physical feeling experienced by the subject during or immediately after the treatment, or one or more characteristics of fecal matter excreted by the subject during or following the treatment.

In some embodiments, the feedback is received from a human, such as from the subject, a medical practitioner or medical professional treating the subject, or a care-giver of the subject. In some embodiments, the feedback is received from a sensor, as described in further detail hereinbelow.

In some embodiments, the processor 110 is further configured to assign a weight, or a reliability score, to such feedback, as described in further detail hereinbelow.

In some embodiments, processor 110 is configured to electronically obtain an initial recommendation for an initial recommended treatment protocol for the subject. In some embodiments, the initial recommendation may be a default initial recommendation. In some embodiments, the initial recommendation may be based on at least one selected characteristic included in the subject data. In some embodiments, the initial recommendation may be based on data included in the database 108, for example data relating to other subjects sharing the selected characteristic(s) with the subject.

In some embodiments, processor 110 is configured to electronically obtain an updated recommendation for an updated recommended treatment protocol for the subject, based on received feedback relating to a response of the subject to a previously used treatment protocol, on at least one characteristic included in the subject data and/or on data included in the database 108, for example data relating to other subjects sharing the characteristic with the subject or sharing the experienced response with the subject.

The updated recommendation may change one or more parameters of the vibration protocol or of the treatment protocol, relative to a previous recommendation. For example, the updated recommendation may change the vibration frequency, the delay time until starting the vibration protocol, the duty cycle, the segment in the GI tract in which the capsule is intended to vibrate, the length of the vibration time in each vibration cycle, the rest time of each vibration cycle, and/or the vibration intensity.

The system 100 further includes a first vibrating ingestible capsule 114a, adapted to implement a first vibration protocol for delivering vibrations, or mechanical stimulation, to a wall of the GI tract of the subject thereby to treat the gastrointestinal disorder of the subject, the first vibration protocol forming part of a first treatment protocol for the subject. The system further includes at least one second programmable vibrating ingestible capsule 114b, adapted to be programmed to implement a second vibration protocol delivering vibrations, or mechanical stimulation, to a wall of the GI tract of the subject thereby to treat the gastrointestinal disorder of the subject, the second vibration protocol forming part of a second treatment protocol for the subject. As explained in further detail hereinbelow, in some embodiments, the first and/or second vibration protocols and/or treatment protocols may be identical to, or may be based on, recommended vibration protocols and/or treatment protocols electronically obtained by processor 110.

Each of capsules 114a and 114b may include a sensor module including one or more sensors; a timer; an intermittently activated vibration engine; a processor, functionally associated with the sensor(s) in the sensor module, with the timer, and with the vibration engine; a receiver or transceiver functionally associated with the processor; and at least one power source providing power to the sensor module, the timer, the vibration engine, the processor, and/or the receiver/transceiver.

In some embodiments, the sensors included in the sensor module may sense conditions in the vicinity of the capsule. As such, the sensors may include: a pH sensor adapted to sense the pH in the vicinity of the capsule; a light sensor adapted to sense a degree of illumination in the vicinity of the capsule; a pressure sensor adapted to sense pressure applied to the capsule; and/or an orientation sensor, such as an accelerometer, adapted to sense the three dimensional orientation of the capsule.

The power source of capsules 114a and 114b may be any suitable power source, such as, for example, one or more alkaline or silver oxide batteries, lithium batteries, primary batteries, rechargeable batteries, capacitors and/or super capacitors.

In some embodiments, the capsules 114a and 114b may be substantially as described in U.S. Patent Application Publication No. 2015/0073315 and in U.S. Pat. No. 9,078,799 which are incorporated by reference as if fully set forth herein.

In some embodiments, first vibrating ingestible capsule 114a may be a programmed vibrating ingestible capsule, programmed, for example at a time of manufacturing thereof, to implement a specific vibration protocol as the first vibration protocol. In other embodiments, the first vibrating ingestible capsule 114a is a first programmable vibrating ingestible capsule 114a, adapted to be programmed to implement the first vibration protocol.

In some embodiments, the first treatment protocol may be a default treatment protocol, used as the standard initial treatment protocol for subjects suffering from any disorder, or from a specific disorder, of the gastrointestinal tract, and may define a default vibration protocol as the first vibration protocol.

A capsule control unit 116, functionally associated with processor 110 and with at least one programmable vibrating ingestible capsule, is adapted to receive a vibration protocol and to program a programmable vibrating ingestible capsule to implement the received vibration protocol. In some embodiments, the capsule control unit 116 is adapted to receive a treatment protocol including treatment procedures and a vibration protocol and to program the programmable vibrating ingestible capsule to implement the received vibration protocol.

In some embodiments, capsule control unit 116 may include a dedicated processor; a programming module; a verification and activation module; and/or a transceiver or other communication module. The capsule control unit may further include at least one power source providing power to components of the capsule control unit.

In some embodiments, the capsule control unit 116 further includes a user interface, adapted to provide output to the subject or to another user associated with the subject, such as a medical practitioner or care giver. In some such embodiments, the capsule control unit 116 may prompt the subject, via the user interface, to ingest one or more capsules in accordance with the treatment protocol received by the capsule control unit.

Capsule control unit 116 may be any suitable control unit, including a suitably programmed computing device such as a smartphone, a tablet computer, laptop computer, desktop computer, and the like, or may be a dedicated control unit, e.g., a stand-alone control unit or a control unit forming part of another medical device.

In system 100, capsule control unit 116, or a dedicated processor thereof, is adapted to receive from processor 110 the second treatment protocol, for example via a transceiver of the capsule control unit 116, and to program the second programmable vibrating ingestible capsule 114b to implement the second vibration protocol defined in the second treatment protocol. In some embodiments, in which first vibrating ingestible capsule 114a is programmable, capsule control unit 116 may be further adapted to similarly receive the first treatment protocol, from processor 110 or from another source, and to program the first vibrating ingestible capsule 114a to implement the first vibration protocol defined in the first treatment protocol.

In some embodiments, the programming module of capsule control unit 116 is configured to receive the second vibration protocol from the processor of the capsule control unit, and to program a processor of second programmable vibrating ingestible capsule 114b to implement the second vibration protocol upon activation thereof or upon ingestion of the second vibrating ingestible capsule. Similarly, in embodiments in which first vibrating ingestible capsule 114a is programmable, the programming module of capsule control unit 116 is configured to receive the first vibration protocol from the processor of the capsule control unit, and to program a processor of first vibrating ingestible capsule 114a to implement the first vibration protocol upon activation thereof or upon ingestion of the first vibrating ingestible capsule.

In some embodiments, the programming module of capsule control unit 116 may include a transmitter, or may be functionally associated with a transmitter, for transmission of the first and/or second vibration protocol to a receiver/transceiver of capsules 114a and/or 114b, for example using a short range wireless communication method.

In some embodiments, the programming module of capsule control unit 116 transmits the vibration protocol to the capsule 114a or 114b as a sequence of parameter signals, such as digits, indicating time frames from activation or from ingestion and vibration parameters to he used at those time frames. In some embodiments, the programming module of capsule control unit 116 transmits the vibration protocol to the capsule 114a or 114b as executable code to be used by the processor of the capsule to automatically activate the vibration engine thereof in accordance with the vibration protocol.

In some embodiments, a memory element within the capsule 114a or 114b includes multiple vibration protocols which may be effected by the capsule, and the programming module of capsule control unit 116 transmits to the capsule an indication of a specific one of the multiple vibration protocols to be used, such as a vibration protocol identifier.

In some embodiments, the activation module of the capsule control unit 116 is configured to activate the first and/or second programmable vibrating ingestible capsule for operation.

In some cases, the activation includes activating the capsule to identify ingestion thereof by the subject, and subsequently to begin implementation of the vibration protocol programmed therein. In other embodiments, activation of the capsule includes immediate activation of the timer to start counting time till activation of the vibration engine. Such embodiments assume that the capsule is activated shortly before the subject ingests the capsule. In yet other embodiments, activation of the capsule occurs following ingestion of the capsule by the subject, by providing to the ingested capsule a remote activation signal.

In some embodiments, the activation module of capsule control module 116 includes a transmitter, or is functionally associated with a transmitter or transceiver, and activates the capsule by providing an activation signal thereto.

In some embodiments, the activation module also includes a verification module, configured to verify that the capsule received the vibration protocol transmitted thereto and is capable of effecting the vibration protocol without error. In some embodiments, the verification module includes, or is functionally associated with a receiver, receiving from the capsule a verification signal indicating that the capsule has received the vibration protocol. In some embodiments, the verification module includes a vibration sensor, sensing the capsule vibrating in accordance with a specific vibration pattern indicative of verification thereof.

In some embodiments, the processor 110 and the capsule control unit 116 are functionally associated with a decision maker 118, which is adapted to receive, for example from processor 110, a suggestion or recommendation for a treatment protocol or a vibration protocol, and to approve, reject, or modify the suggested or recommended protocol for treatment of the subject.

In some embodiments, the decision maker may be a human decision maker, such as a medical practitioner or treating gastroenterologist, who may receive the suggested or recommended treatment protocol or vibration protocol by the protocol being presented on a display visible to the human decision maker, or by receiving an electronic message, such as an email message, specifying the recommended or suggested treatment protocol or vibration protocol.

The human decision maker may approve, reject, or modify the received recommended treatment protocol or vibration protocol by interacting with a user interface 104 of one of input modules 102, or by interacting directly with capsule control unit 116, for example with an input module or user interface thereof.

In other embodiments, the decision maker 118 is an electronic decision maker, such as a suitably equipped computer or server, which is adapted to electronically receive the suggested or recommended treatment protocol or vibration protocol, and to approve, reject, or modify the suggested or recommended treatment protocol or vibration protocol. In some embodiments, the logic applied by the electronic decision maker may be learned over time, for example based on the results that similar treatment had for other subjects. In some embodiments, the electronic decision maker may include an artificial intelligence component.

In some embodiments, decisions made by an electronic decision maker are limited to be within certain limitations, or within a "self adapting zone" predefined by a human decision maker, such as safety regulations defined by a manufacturer of the capsule and/or medical limitations defined by a medical practitioner. For example, the manufacturer may indicate that the frequency of vibrations has an upper limit of 1000 Hz, in which case the decision maker will not permit, or approve, any protocol requiring vibration at a frequency greater than 1000 Hz. As another example, a medical practitioner may indicate that no changes can be made to treatment procedures, in which case the electronic decision maker would make decisions relating to the vibration protocol, but would defer any decisions relating to the treatment procedures to a human decision maker, for example via an electronic message.

In some embodiments, the limitations are based on the structure and/or functionality of the capsule, such as safety limitations defined by the manufacturer. In such embodiments, the same limitations apply to multiple subjects, and multiple capsules. In some embodiments, the limitations are defined by the medical practitioner based on the medical state of the subject, and are specific to the subject being treated. Such limitations may be provided as input by the medical practitioner, for example as part of the subject data stored in the subject profile.

In some embodiments, the electronic decision maker may be functionally associated with the capsule control unit 116, and may transmit the approved or modified treatment protocol or vibration protocol directly to the capsule control unit 116. In other embodiments, the electronic decision maker provides the approved or modified treatment protocol or vibration protocol to processor 110, which may transmit the treatment protocol to capsule control unit 116 as described hereinabove.

In some embodiments, processor 110 and/or subject profile 106 are further associated with at least one sensor 120, which is adapted to sense, and provide to processor 110 and/or to subject profile 106, information regarding a vibrating ingestible capsule being expelled from the body of the subject. In some embodiments, the sensor comprises a toilet-bowl mounted sensor. The toilet bowl mounted sensor may be any suitable sensor, such as any one of the inventive sensors described hereinbelow with reference to FIGS. 3A to 8, or a toilet-bowl mounted sensor known in. the art, for example as described in U.S. Patent Application Publication No. 2009/0326514, which is hereby incorporated by reference.

The information provided by sensor 120 may include a time at which the vibrating ingestible capsule was expelled from the body of the subject, an identification of the expelled capsule, and/or information regarding characteristics of excrement expelled from the body of the subject.

Figure 2B:
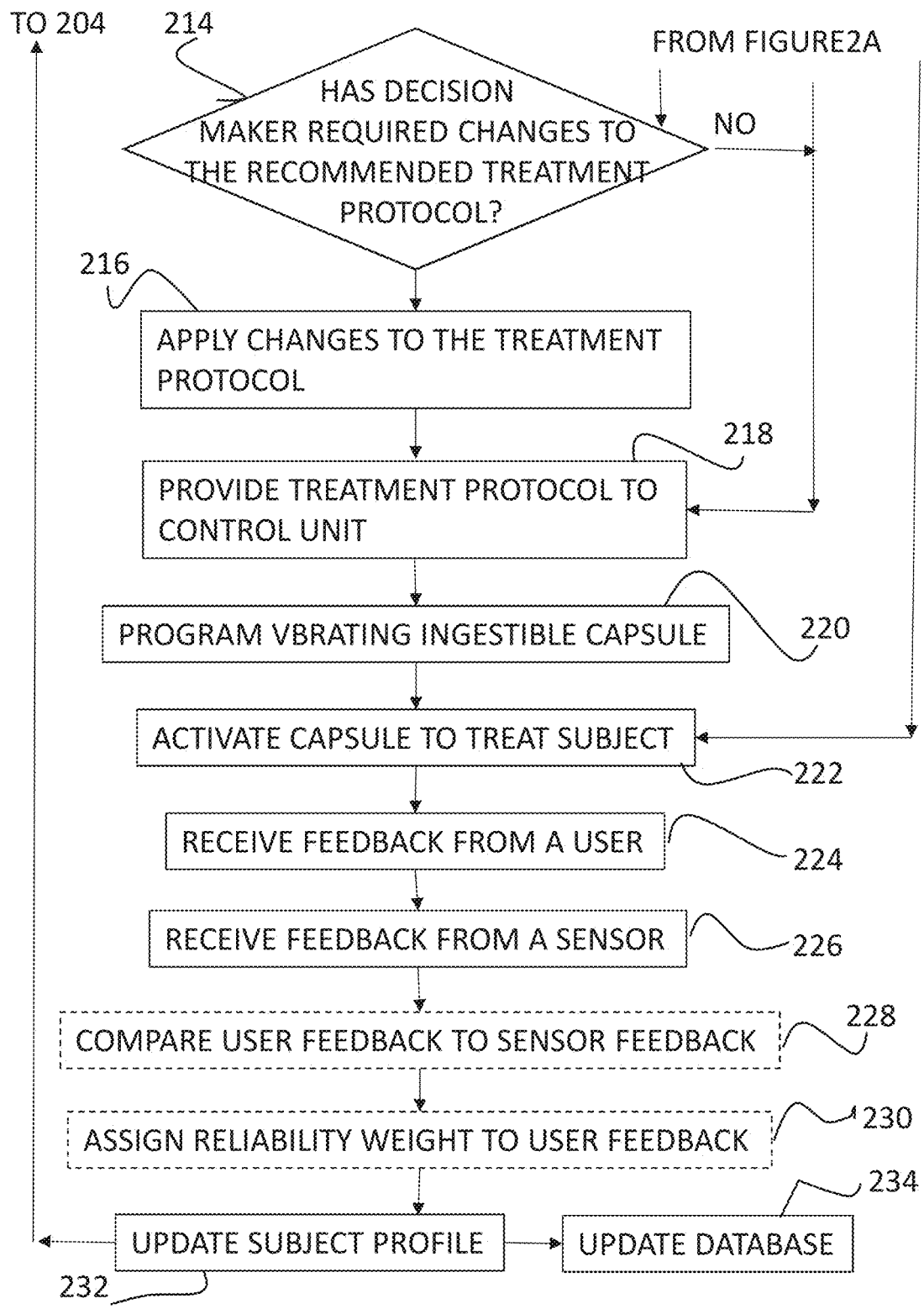

Reference is now additionally made to FIGS. 2A and 2B, which, together, are a schematic flowchart of a method for treatment of a disorder in the gastrointestinal tract of a subject according to the present invention, the method utilizing the inventive system of FIG. 1.

As seen, and as described in further detail hereinbelow, the method may start step 200, at step 218, or at step 222.

In some embodiments, the method begins at step 200, by obtaining initial input including subject data for a subject to be treated using the method. The subject data typically includes demographic information and/or medical history information for the subject, required for initiating subject profile 106. In some embodiments, the input may additionally include information relating to other subjects, such as information required for creating or updating database 108. In some embodiments, the input may further include limitations defining a "self adapting zone" for an electronic decision maker, as described hereinabove.

As mentioned hereinabove with reference to FIG. 1, the input may be received from the subject, from a medical facility or medical practitioner treating the subject, or from a caretaker of the subject. In some embodiments, the input is provided to input module 102 via a user interface 104 which is local to system 100, while in other embodiments the input may be provided via a remote user interface 104, and communicated to input module 102 or to processor 110 using a suitable communication method.

At step 202, a subject profile, such as subject profile 106 described hereinabove with respect to FIG. 1, is generated for the subject, for example by processor 110, based on the input relating to the subject.

Turning to step 204, it is seen that a recommendation for a recommended treatment protocol for the subject is obtained. In some embodiments, the recommendation is electronically obtained by processor 110. In some embodiments, the recommendation is based on information included in the subject profile 106.

For example, in an initial treatment round, the subject profile may indicate that the motility in the subject's digestive system is slower than the motility of the average digestive system, such that the food reaches the colon after a longer time than the average 10 hours. In such embodiments, processor 110 may recommend a treatment protocol having a long enough activation delay time so as to ensure that the capsule vibrates when it has reached the subject's large intestine, and does not vibrate prematurely.

In some embodiments the recommendation may also be based on data obtained from database 108, the data relating to one or more other subjects. For example, in an initial treatment round, the subject profile 106 may indicate that the subject is a female aged 55. Processor 110 may access database 108 to identify treatment protocols and/or vibration protocols that were successfully used to treat other females having similar ages, for example aged 50-60. One such identified protocol may be suggested as the recommended treatment protocol for the subject, or a new treatment protocol, including characteristics of a number of such identified protocols, may be generated as the recommended treatment protocol for the subject.

As described in further detail hereinbelow, the method described herein is iterative, and subject profile 106 may be updated to reflect the response of the subject to treatment with a specific treatment protocol. As such, in subsequent treatment rounds, processor 110 may use data relating to such responses when generating the recommendation for the next treatment protocol to be used.

Returning to the example provided above, the subject profile 106 may, in a later treatment round, indicate that the subject's condition did not improve when treated with a vibration protocol providing capsule vibration at a frequency of 150 Hz. The processor may then recommend an updated vibration protocol having a different vibration frequency.

Selection of a subsequent treatment protocol may also be based on data from the database, relating to at least one other user. In the example above in which the subject's condition did not improve when treated with a vibration protocol providing capsule vibration at a frequency of 150 Hz, the processor may, when identifying in database 108 potential treatment protocols, limit the identified protocols to ones providing vibration at a higher frequency, provided that the higher frequency is within a predetermined permissible range for the capsule and/or for the specific subject, such as up to 250 Hz. As another alternative, the processor may identify treatment protocols that were successfully used to treat females aged 50-60 which did not respond well to treatment with capsule vibration at a frequency of 150 Hz.

When updating the vibration protocol or treatment protocol in a second or subsequent treatment round, the updated recommended treatment protocol may change one or more parameters of the vibration protocol or of the treatment protocol, relative to a previous recommendation. For example, the updated recommendation may change parameters of the vibration protocol, such as the vibration frequency, the delay time until starting the vibration protocol, the duty cycle, the segment in the GI tract in which the capsule is intended to vibrate, the length of the vibration time in each vibration cycle, the rest time of each vibration cycle, and/or vibration intensity, and/or parameters of the treatment procedures, such as the frequency at which a capsule should be ingested, the time of day at which the capsule should be ingested, and/or whether the capsule should ingested with or without food.

As seen at step 206, the processor 110 may then check whether or not the obtained recommended treatment protocol is significantly different from a previously used treatment protocol. Naturally, in an initial iteration of the method described herein, step 206 would be obviated. In some embodiments, a treatment protocol would be considered 'significantly different' from another treatment protocol if the vibration protocol and/or the treatment procedures defined by the treatment protocol, or any portion thereof, is not in the range of allowed treatment protocols and/or characteristics defined for the subject, as described hereinabove.

If the recommended treatment protocol is significantly different from the treatment protocol used in a previous round of treatment, at step 208 the recommended treatment protocol is provided by processor 110 to decision maker 118, which may be a human decision maker, such as a medical practitioner treating the subject, or may be an electronic decision maker, as described hereinabove.

As seen at step 210, input from the decision maker is received by processor 110. The decision maker may require that the recommended treatment protocol be modified prior to treating the subject, or may indicate that the recommended treatment protocol, or a similar treatment protocol based on the recommended treatment protocol, should not be used for the subject, and such requirements may be provided as the input. In embodiments in which the decision maker is human, the input may be provided via user interface 104 and input module 102.

At step 212, processor 110 checks whether or not the decision maker has approved treating the subject using a treatment protocol which is based on the recommended treatment protocol. If processor 110 identifies that the decision maker has not approved use of a treatment protocol based on the recommended protocol, the method returns to step 204 for selection of another recommended treatment protocol.

Otherwise, if processor 110 identifies that the decision maker approved use of the recommended treatment protocol, at step 214 the processor checks whether or not the decision maker has required making any changes to the recommended treatment protocol in order to obtain the treatment protocol to be used.

As seen at step 216, if such changes are required, processor 110 applies the changes to the recommended treatment protocol, thereby to generate the treatment protocol to be used. Once the treatment protocol is generated at step 216, the generated treatment protocol, or, in some embodiments, only the vibration protocol defined thereby, is provided by processor 110 to capsule control unit 116 at step 218.

Alternately, if no changes were required to the recommended treatment protocol (at step 214), or if the recommended treatment protocol is not significantly different from the treatment protocol used in an immediately previous round of treatment (at step 208), the treatment protocol to be used is set to be identical to the recommended treatment protocol, and the treatment protocol, or only the vibration protocol defined thereby, is provided by processor 110 to capsule control unit 116, at step 218.

As another alternative, the method may start from step 218, for example by providing to the capsule control unit 116 a default treatment protocol or a default vibration protocol to be used in a first treatment iteration. In such embodiments, the default treatment protocol or the default vibration protocol may be provided by the manufacturer of the capsule or by a medical practitioner for any subject beginning treatment using the system of FIG. 1, regardless of the subject's profile or of any data collected in the database regarding other subjects. In other embodiments, the method may begin with steps 200 and 202 so as to create the subject profile, and may then proceed directly to step 218 wherein the default treatment protocol or default vibration protocol is provided to the capsule control unit 116.

Once the capsule control unit 116 has received the vibration protocol to be used, possibly as part of the treatment protocol to be used, at step 220 the capsule control unit 116 programs a programmable vibrating ingestible capsule, such as capsule 114a or 114b, to implement the vibration protocol upon activation of the capsule or upon ingestion thereof, substantially as described hereinabove with respect to FIG. 1. In some embodiments, the capsule control unit 116 also provides output to the subject or to a caretaker thereof, for example via a display or other user interface, the output indicating the treatment procedures defined in the treatment protocol to be used.

As seen at step 222, once the programmable vibrating ingestible capsule (e.g. 114a or 114b) has been programmed to implement the vibration protocol, the capsule is activated, for example by the activation module of capsule control unit 116 as described hereinabove, and is provided to the subject for ingestion thereof, thereby to treat the subject. As explained hereinabove, the subject or a caretaker thereof is notified of the treatment procedures, and is instructed to ingest the programmed capsule in accordance with the treatment procedures defined in the treatment protocol being used.

In some embodiments, the capsule may be provided to the subject for ingestion without previous activation thereof. In such embodiments, the capsule may be activated while it is within the gastrointestinal tract of the subject, for example by providing a remote signal, from the exterior of the subject's body to a receiver of the capsule.

In some embodiments, the first vibrating ingestible capsule used to effect the first iteration of treatment is not a programmable capsule, but rather a programmed capsule, programmed to implement a specific vibration protocol, such as the default vibration protocol, for example as described hereinabove with reference to capsule 114a of FIG. 1. In some such embodiments, the method may begin at step 222, by activation of the programmed capsule and treatment of the subject therewith. In other embodiments, the method may begin with steps 200 and 202 so as to create the subject profile, and may then proceed directly to step 222 wherein the programmed capsule is activated and used to treat the subject.

During treatment of the subject, or following such treatment, processor 110 receives feedback from a user, which may be the subject, a medical practitioner treating the subject, and/or a caretaker of the subject, regarding the subject's response to the treatment, as seen at step 224. In some embodiments, the feedback is provided to processor 110 via user interface 104 and input module 102.

In some embodiments, the feedback limy indicate times at which the subject experienced bowel movements during or following treatment in accordance with a specific treatment protocol, or a number of spontaneous bowel movements (SBM) or complete spontaneous bowel movements (CSBM) experienced during or following the treatment.

In some embodiments, the feedback may indicate a physical feeling experienced by the subject during or following treatment in accordance with a specific treatment protocol, such as a feeling of complete evacuation following a bowel movement, straining, bloating, gas, flatulence, pain during bowel movements, pain at times other than during a bowel movement, or other adverse events occurring during or following the treatment. For example, the subject may provide feedback indicating that vibration was felt when the capsule was passing through the rectal area of the subject, or that stomach pains were relieved following the treatment.

In some embodiments, the feedback may indicate treatment procedures used by the subject during implementation of the treatment protocol, such as, for example, a time of day at which a vibrating ingestible capsule was ingested.

In some embodiments, the feedback may indicate at least one characteristic of fecal matter excreted by the subject during or following the treatment in accordance with the treatment protocol. For example, the subject may provide feedback indicating the Bristol stool measure of a bowel movement following the treatment.

At step 226, the processor 110 may receive feedback from one or more sensors 120. In some embodiments, a sensor 120 is mounted in the toilet-bowl, and provides information regarding expelling of the vibrating ingestible capsule from the body of the subject. In some embodiments, the information includes an indication of a time at which the vibrating ingestible capsule was expelled from the body of the subject. In some embodiments, the information includes an identification of the expelled capsule. In some embodiments, the information includes information regarding fecal matter expelled by the subject, such as tier example a Bristol stool measure of the fecal matter, as described hereinbelow.

As discussed hereinabove with respect to FIG. 1, a toilet-bowl mounted sensor 120 may be any suitable sensor known in the art, such as that described in U.S. Patent Application Publication No. 2009/0326514, or may be an inventive sensor as described hereinbelow with reference to FIGS. 3A to 7. An exemplary method by which the inventive sensors of FIGS. 3A to 7 obtain and provide feedback to processor 110 is described hereinbelow with respect to FIG. 8.

In some embodiments, at step 228 processor 110 may optionally compare, or cross-reference, the feedback provided by the user at step 224 to the feedback received from the sensor at step 226, and may assign a reliability weight to the feedback from the user and/or from the sensor based on the results of such comparison, as seen at step 230.

For example, the processor 110 may compare the times at which the subject reported to have had bowel movements, and the time at which the sensor reported that the capsule was expelled. If the subject did not report a bowel movement at the time that the capsule was expelled, this is indicative of the subject not providing accurate feedback, and as such the sensor based feedback would be assigned a higher reliability weight than the feedback received from the subject.

At step 232, the processor 110 updates the subject profile 106 based on the feedback provided by the subject, the medical practitioner, and/or the caretaker at step 224, and/or based on the feedback provided by the sensor 120 at step 226. In embodiments in which the subject and/or sensor feedback is assigned a reliability weight at step 230, the reliability weight is taken into consideration when updating the subject profile, such that a greater significance is given to the more reliable feedback.

Subsequently, the method returns to step 204, and an updated treatment protocol recommendation for the subject is obtained based on the updated user profile and based on data from database 108, which data relates to at least one other subject.

In some embodiments, following updating of the subject profile 106 at step 232, the processor 110 creates or updates an entry in database 108 relating to the subject, for example based on the update subject profile 106, as seen at step 234.

Figure 3A:
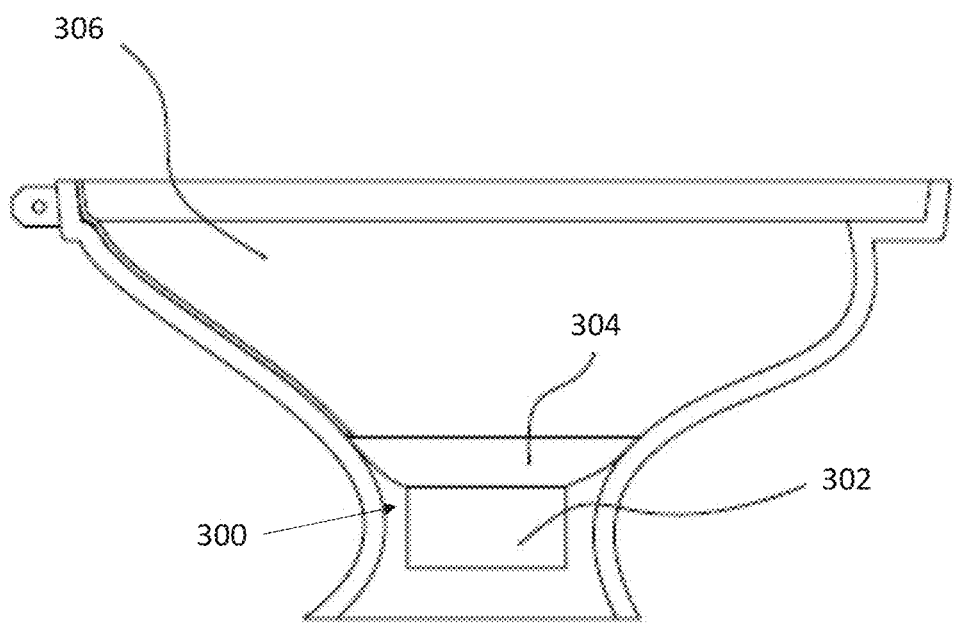
Figure 3B:
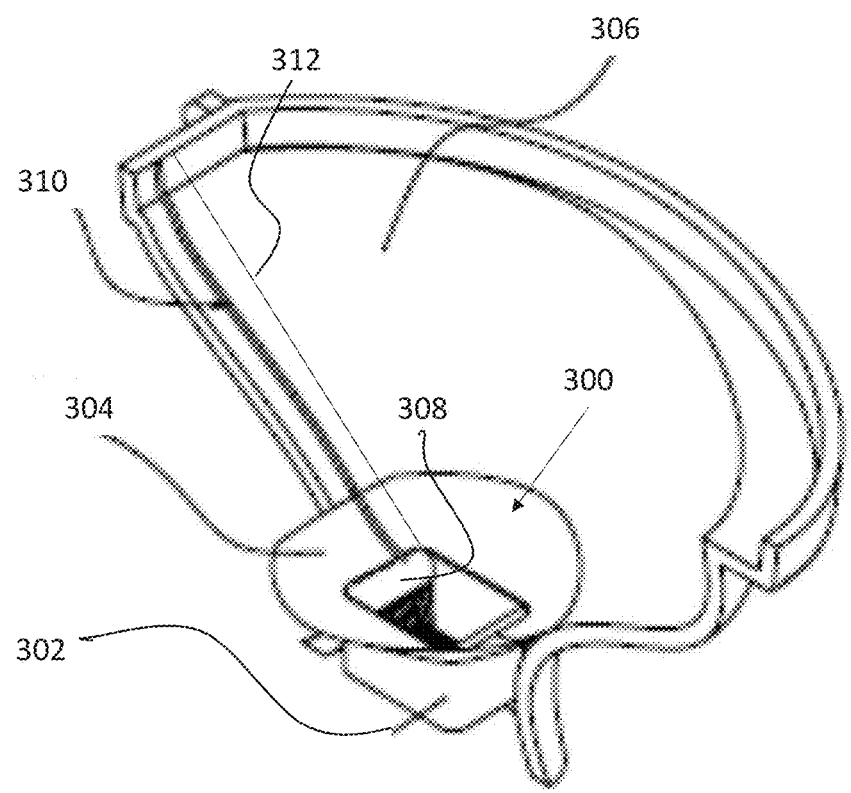

Reference is now made to FIGS. 3A, 3B, and 3C which are, respectively, a partially cut away side plan view, a partially cut away perspective view, and a top plan view of an inventive toilet-bowl mounted sensor 300 for capturing and identifying an ingestible capsule according to the present invention. In some embodiments, the toilet-bowl mounted sensor 300 may form part of the system of FIG. 1, for example as sensor 120.

As seen in FIGS. 3A-3C, sensor 300 includes a receptacle 302 surrounded at a top end thereof by a sealing rim 304. The sensor 300 is adapted to be placed within a toilet bowl 306, at a portion thereof in which sealing rim 304 engages, and seals against, the entire circumference of the toilet bowl, such that any excrement expelled into the toilet bowl would be caught in receptacle 302.

In some embodiments, the receptacle 302 is thrilled of a wire frame or a mesh frame, having gaps or openings large enough to allow water and excrement to pass through, but smaller than the diameter of the capsule to be caught in the receptacle, such that the capsule does not fall through the frame.

Extending along toilet bowl 306, from the exterior thereof to a controller 308 of sensor 300 (described in further detail hereinbelow), is at least one conduit 310 for providing water flow to sensor 300, and at least one wire 312 for providing electrical power to sensor 300 and/or for enabling communication of sensor 300 with a remote device, such as processor 110 of FIG. 1.

Figure 4:
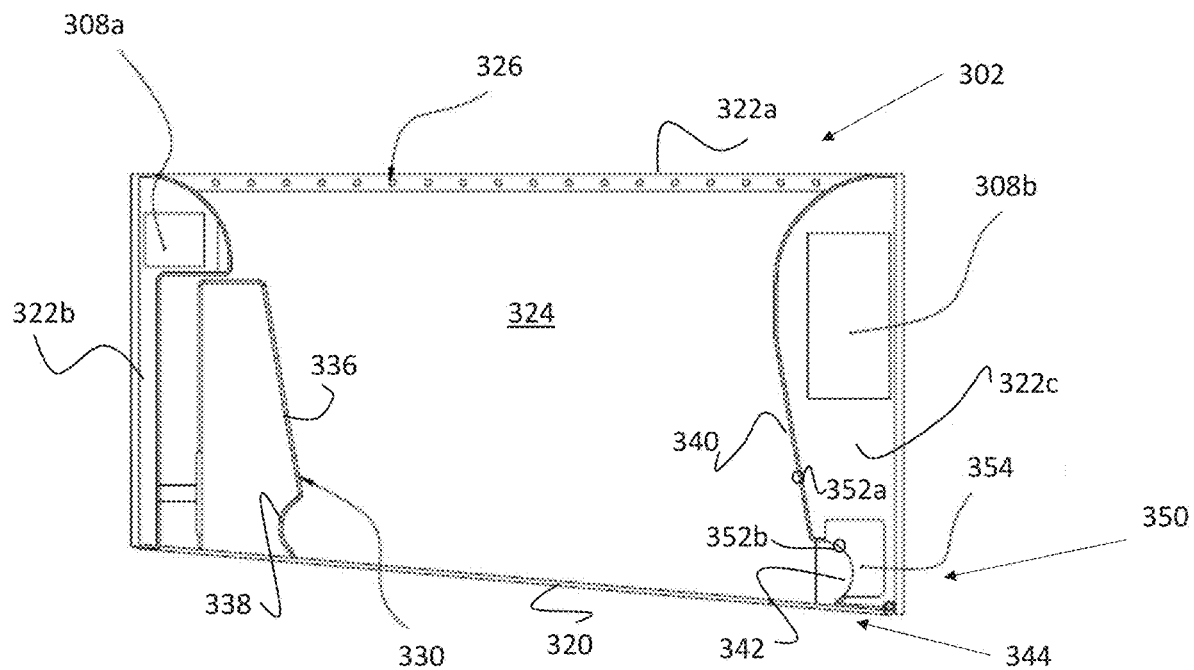
FIG. 4 is a sectional view of another embodiment of a receptacle, forming part of an inventive toilet-bowl mounted sensor according to the present invention, in a stand-by mode.

Reference is now made to FIG. 4, which is a sectional view of an embodiment of receptacle 302 of toilet-bowl mounted sensor 300 in a stand-by mode.

As seen, receptacle 302 has a wire frame bottom surface 320 as described hereinabove, and side walls 322 surrounding a hollow 324. At least one side wall, indicated in FIG. 4 by reference numeral 322a includes a plurality of water jets 326 which receive water from conduit 310 and are adapted to spray water into hollow 324, in order to wash out excrement therefrom.

A pushing mechanism 330, which in some embodiments includes a plurality of wire frame elements 332 (seen clearly in FIG. 5A) connected to one another by a connector surface 334 (seen clearly in FIG. 5A), is disposed within receptacle 302 and is movable relative to one of side walls 322b, as explained in further detail hereinbelow. Pushing mechanism 330 is adapted to move back-and-forth along the receptacle 302 between side walls 322b and 322c, so as to provide mechanical force on excrement in the receptacle for breaking thereof into pieces that can be flushed out of the receptacle via the wire frame bottom 320. In some embodiments, pushing mechanism 330 is further adapted to sense the Bristol stool measure of the excrement in receptacle 302, for example by sensing the three exerted by the motor driving the pushing mechanism 330 for breaking down the excrement.

A side of pushing mechanism distal to the side wall 322b includes a diagonal section 336 terminating in a generally hemispherical ingress 338, which, together with a corresponding diagonal section 340 and generally hemispherical ingress 342 formed in an opposing side wall 322c of receptacle 302 are adapted for capturing a vibrating ingestible capsule and for measurement and identification thereof, as described in further detail hereinbelow.

Disposed beneath ingress 342 is a capsule releasing mechanism 344, adapted, following capturing of an expelled capsule and identification thereof, to release the capsule from receptacle 302 for flushing thereof down the toilet. In some embodiments, releasing mechanism 344 comprises a hatch 346 (seen clearly in FIG. 7), hingedly connected to side wall 322c, which is adapted to open and release a captured capsule following identification thereof, and to close back immediately following removal of the capsule.

It will be appreciated that though in the illustrated embodiment the bottom surface 320 is slanted toward side wall 322c and ingress 342, so as to allow gravity to assist a capsule in arriving at its capturing location as described in further detail hereinbelow, in some embodiments the bottom surface 320 may be horizontal and perpendicular to the side walls 322b and 322c.

Included within side wall 322c, adjacent to ingress 342, is a capsule identification mechanism 350, which may include one or more sensors 352, a vision system 354, a communication system, and/or a weighing mechanism, for measuring the dimensions and/or weight of a captured capsule, and/or for uniquely identifying the capsule.

As described in further detail hereinbelow, sensors 352 may be contact sensors or distance sensors adapted to sense contact between, or a distance between, diagonal sections 336 and 340 and/or contact between a capsule captured between ingresses 338 and 342 and the ingress walls.

Vision system 354 has a field of view, and is typically adapted to view a wall of a captured capsule via the field of view, so as to uniquely identify the capsule. In some embodiments, the vision system may include a barcode reader adapted to identify a barcode printed onto the exterior of a captured capsule, a QR-code reader adapted to identify a QR-code printed onto the exterior of a captured capsule, an OCR mechanism adapted to scan and interpret text or an identification number printed onto the exterior of a captured capsule, or an image capturing and analysis mechanism adapted to capture an image of the exterior of the capsule and to analyze the captured image thereby to identify the capsule or a manufacturer thereof.

In some embodiments, the communication system includes an RFID tag reader adapted to read an RFID tag mounted on the exterior of a captured capsule, thereby to identify capsule. The communication system may he incorporated in the vision system or may he separate therefrom.

The weighing mechanism may be disposed on bottom surface 320 of the receptacle 302, preferably adjacent to ingress 342, so as to weigh a capsule captured between ingresses 338 and 342, as described in further detail hereinbelow. In some embodiments, weighing mechanism is mounted onto releasing mechanism 344.

Controller 308 of receptacle 302 may be disposed on or within one or more of side walls 322 and is adapted to control movement, and in some embodiments sensing capabilities, of pushing mechanism 330, and to control operation of identification mechanism 350 and of releasing mechanism 344. Additionally, controller 308 is adapted to provide power to pushing mechanism 330, releasing mechanism 344 and identification mechanism 350.

In some embodiments, controller 308 is adapted to receive input from weighing mechanism 344 and/or from identification mechanism 350, so as to identify that a capsule has been captured, and the dimensions, weight, and/or identity of the captured capsule. In some embodiments, controller 308 includes a clock for identifying a time at which a capsule was captured and/or identified.

Typically, controller 308 is adapted to communicate with a remote location, such as processor 110, via a communication module forming part of the controller and/or via a communication wire 310 extending from receptacle 302, along toilet bowl 306 to the remote location. In some embodiments, the controller 308 may communicate the time at which the capsule was captured, and information regarding the capsule, such as its dimensions, weight, and/or identity, to the remote location, for use thereof. For example, in the embodiment of FIGS. 1 and 2, the information provided by the controller 308 may be used to identify a time that the capsule has spent in the GI tract of the subject, or an order at which a plurality of ingested capsules were expelled.

In some embodiments, the controller 308 may further communicate information relating to characteristics of the expelled fecal matter, such as a Bristol stool measure thereof, as sensed by pushing mechanism 330 or by the motor driving the pushing mechanism. In some such embodiments, the controller 308 only communicates the information relating to the fecal matter if a capsule was captured, or if a capsule of a specific type was captured.

In the embodiment illustrated in FIG. 4, controller 308 has a first portion 308a disposed within side wall 322b and adapted to control and to provide power to pushing mechanism 330, and a second portion 308b disposed within side wall 322c and adapted to control and to provide power to releasing mechanism 344 and identification mechanism 350. However, any other arrangement of controller 308 is considered within the scope of the invention.

Figure 5B:
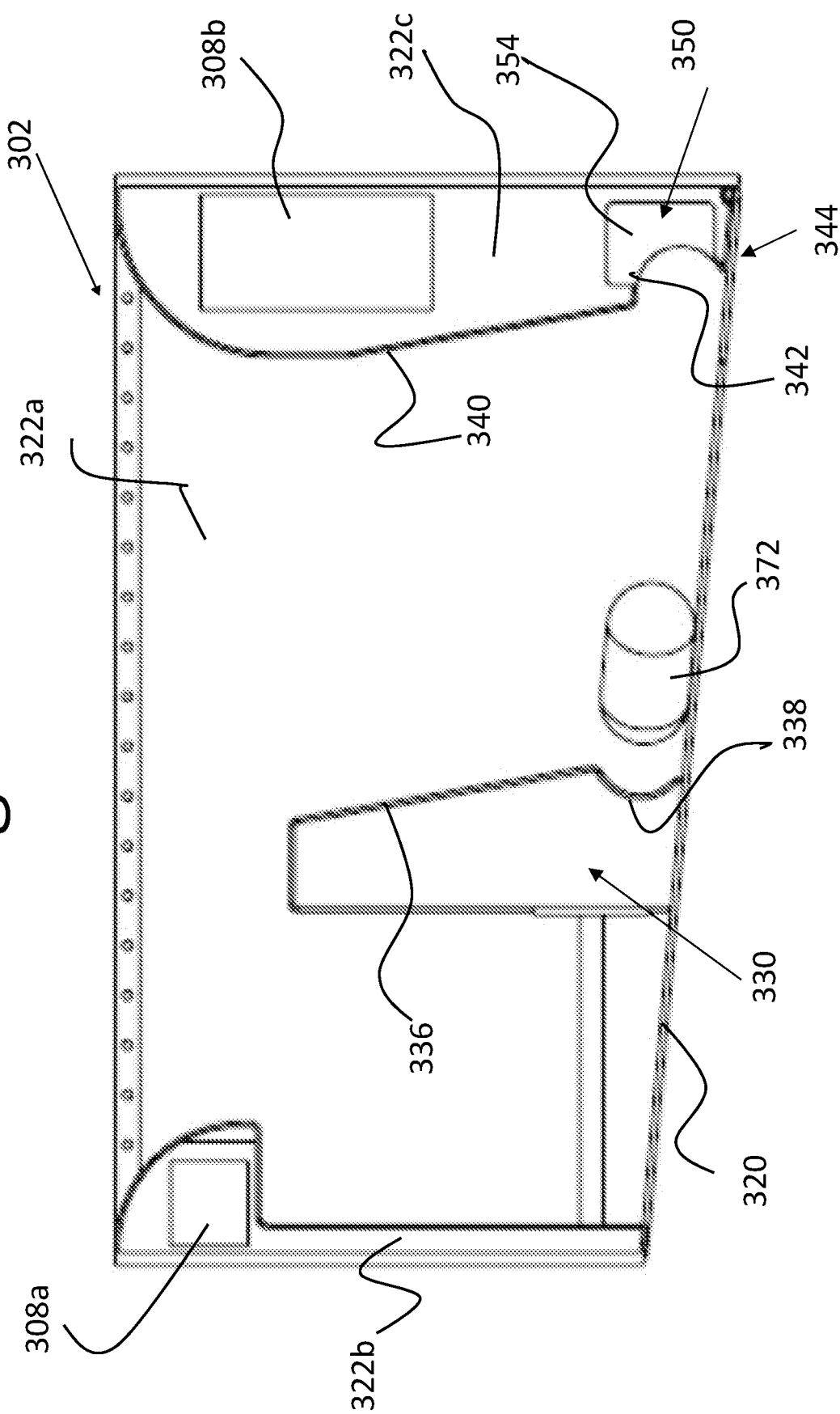

Reference is now made to FIGS. 5A and 5B, which are, respectively, a perspective view and a sectional view of the receptacle 302, in an operational mode. As seen, pushing mechanism 330 is being pushed away from side wall 322b and toward side wall 322c, as indicated by arrow 370. A vibrating ingestible capsule 372, which was expelled from the body of a subject together with fecal matter thereof, is caught by receptacle 302, and may be pushed by pushing mechanism 330 toward ingress 342 and identification mechanism 350. In some embodiments, capsule 372 is generally ovoid, is symmetrical about a longitudinal axis 374, and has a generally circular cross-section in a direction perpendicular to axis 374.

It will be appreciated that pushing mechanism 330 may be pushed in the direction of arrow 370 and back in the opposite direction multiple times, so as to break down fecal matter caught in receptacle 302 for removal thereof via bottom surface 320. In some embodiments, motion of pushing mechanism 330 is accompanied by water spray from jets 326 for washing away fecal matter and cleaning of the capsule, prior to pushing and/or capturing thereof.

Reference is now made to FIG. 6, which is a partial sectional view of receptacle 302 in a capsule capturing mode. As seen in FIG. 6, pushing mechanism 330 is pushed distally from side wall 322b until it engages side wall 322c, such that diagonal sections 336 and 340 engage one another, and such that the capsule 372 is trapped between ingresses 338 and 342. It is a particular feature of the present invention that the arrangement of the wire frame of bottom surface 320, and ingress 338 of pushing mechanism 330, cause capsule 372 to be captured such that longitudinal axis 374 is generally parallel to side wall 322c, and such that the circular cross section of the capsule substantially fills the circular cross-section formed by ingresses 338 and 342.

It is a particular feature of the teachings herein that capturing of the capsule, results in measurement of its dimensions. Specifically, sensors 352 of the identification mechanism 350 identify the dimensions of the capsule. Sensors 352a mounted along section 340 identify whether or not diagonal sections 336 and 340 engage one another—if the diagonal sections do not engage one another when the capsule is captured, the capsule has a greater circumference than that of the circular cross section of the cavity between ingresses 338 and 342. Sensors 352b mounted along ingress 342 identify whether or not the circumference of the capsule engages the ingress wall—if the circumference of the capsule does not engage the ingress walls when the capsule is captured, the capsule has a smaller circumference than that of the circular cross section of the cavity between ingresses 338 and 342. In some embodiments, weighing mechanism 358, which may be disposed beneath ingresses 338 and 342, identifies the weight of capsule 372 while the capsule is captured.

In some embodiments, the circular cross-section of the cavity between ingresses 338 and 342 may be specifically sized to match the cross section of a particular type of capsule, such that controller 308 may identify, based on input received from sensors 352, whether or not the captured capsule is of the particular type. Additionally, even if the dimensions of captured capsule 372 match the expected dimensions, controller 308 may use the identified weight of the capsule to determine whether the capsule is indeed of the expected particular type. The controller 308 may report capture of the capsule, for example to processor 110, if the capsule has the expected dimensions and weight, and may choose not to report capture of the capsule if it is differently sized or has a different weight.

When the capsule 372 is captured between ingresses 338 and 342, vision system 354 may view a portion of the exterior of the capsule 372 via field of view 355, and may thus uniquely identify the capsule. As described above, in one example, the capsule may have a barcode printed thereon, and the vision system includes a barcode reader adapted to identify the capsule by reading the barcode printed thereon. In another example, the capsule may have a QR-code printed thereon, and the visions system includes a QR-code reader adapted to identify the capsule by reading the code printed thereon. In yet another example, the capsule has a specific logo and/or an identification or serial number printed on the exterior thereof, and vision system 354 includes an OCR mechanism or other mechanism suitable for reading the logo and serial number, thereby to identify the capsule.

In some embodiments, identification of the capsule may alternately or additionally be accomplished by communication system 356. For example, the communication system may include an RFID tag reader, which may identify an RFID tag mounted on the exterior of the captured capsule. Following identification of the capsule, the controller 308 may report capturing of the capsule, and information about the capsule, to a remote location, as described hereinabove. In some embodiments, the controller 308 may report the information only if the capsule is identified as belonging to a specific manufacturer, or as being of a specific type, for example as described hereinabove.

Figure 7:
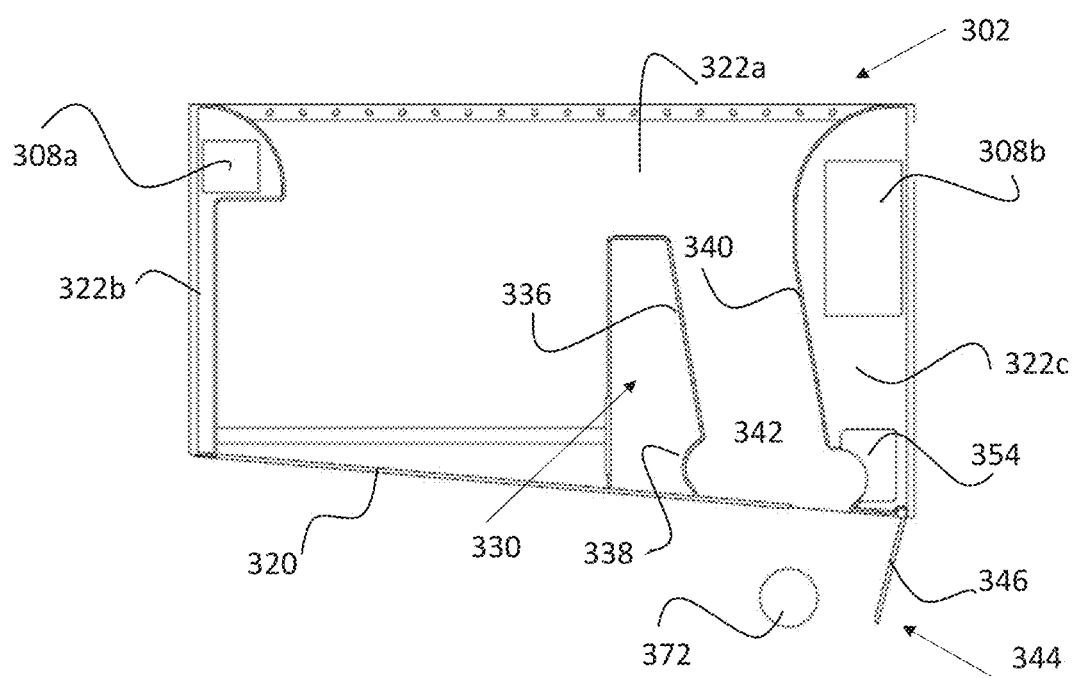
FIG. 7 is a sectional view of the receptacle of FIG. 4 in a capsule releasing mode.

Reference is now made to FIG. 7, which is a sectional view of receptacle 302 in a capsule releasing mode. As seen in FIG. 7, following completion of the capsule identification, pushing mechanism 330 may be displaced away from side wall 322c so as to release the capsule 372 from the hollow between ingresses 338 and 342, and hatch 346 of releasing mechanism 344 may open, for example by rotating downwardly relative to bottom surface 320, so as to allow the capsule 372 to drop out of receptacle 302b, and to be flushed down the toilet. In some embodiments, the releasing mechanism is electrically controlled by controller 308, such that hatch 346 recloses after a predetermined duration during which it is assumed that the capsule has been removed from the receptacle, or after sensors, for example on hatch 346, identify releasing of the capsule.

Reference is now additionally made to FIG. 8, which is a schematic flowchart of a method for capturing and identifying an ingestible capsule that has been expelled into a toilet bowl according to the present invention, the method utilizing the inventive toilet-bowl mounted sensor 300 of any one of FIGS. 3A-7.

At an initial step 400, excrement including an ingestible capsule is captured in a receptacle, such as receptacle 302, of the sensor 300. The pushing mechanism 330 is pushed forward (toward side wall 322c) and back (away from side wall 322c and toward side wall 322b), so as to apply mechanical force to the excrement for breaking down thereof, as seen at step 402.

Subsequently or simultaneously to the breaking action of the pushing mechanism, at step 404, water jets 326 are activated to wash away excrement, which may be removed from the receptacle via the wire frame of bottom surface 320.

In some embodiments, steps 402 and 404 may be repeated for a predetermined number of cycles, a predetermined duration, or until controller 308 determines that there is little or no residual excrement remaining on the capsule or in the receptacle.

At step 406, following removal of excrement and cleaning of the capsule, the pushing mechanism 330 is displaced toward side wall 322c, pushing the capsule in that direction, until the pushing mechanism 330 can move no further.

At step 408, controller 308 assesses whether or not the pushing mechanism has engaged the side wall of the receptacle, and more specifically, whether or not diagonal sections 336 and 340 engage one another, for example using sensors 352a (FIG. 7).

If the pushing mechanism can move no further, but diagonal sections 336 and 340 do not engage one another, this is indicative of the captured capsule having a greater cross-section circumference than the expected capsule, and at step 410 the controller concludes that the captured capsule is not of the expected type. At step 412, the releasing mechanism is operated to release the captured capsule, for example by opening hatch 346 as described hereinabove.

Otherwise, if at step 408 it is determined that the diagonal sections 336 and 340 engage one another, at step 414 controller 308 assesses whether the exterior surface of the captured capsule engages the surface of the cavity between ingresses 338 and 342, for example by using sensor 352b (FIG. 7).

If the capsule does not engage the surface of the cavity when diagonal sections 336 and 340 engage one another, this is indicative of the captured capsule having a smaller cross-section circumference than the expected capsule, and the method continues to step 410 where the controller concludes that the captured capsule is not of the expected type and to step 412 where the capsule is released from the receptacle.

If the capsule is determined to have the expected dimensions, controller 308 may receive from the weighing mechanism information relating to a weight of the captured capsule, and may determine, at step 418, whether or not the measured weight of the capsule matches, or is within a predetermined margin of error, of an expected weight of the capsule. If the measured weight of the capsule does not match the expected weight, the method continues to step 410 where the controller concludes that the captured capsule is not of the expected type and to step 412 where the capsule is released from the receptacle.

Otherwise, the controller concludes that the capsule is of the expected type, and at step 422 the identification mechanism uniquely identifies the capsule, for example by reading a barcode, QR code, unique identification number or string of characters, or an RFID tag located on the exterior surface of the capsule.

At step 424 the controller may report to a remote location, such as processor 110 of FIG. 1, information relating to the capsule, such as the time the capsule was expelled from the body of the user or the time that the capsule was identified by the identification mechanism, and/or the unique identification of the capsule, which information may be used to better understand the subject's response to treatment with the capsule. In some embodiments, the controller may further report information regarding the fecal matter, such as a Bristol stool measure thereof, as identified by the pushing mechanism and as described hereinabove. As discussed in detail hereinabove, the reporting may be carried out by wired or wireless communication between the controller 308, or another portion of the sensor 300, and the remote location.

Subsequently or in parallel to such reporting, the capsule is released from the receptacle, at step 412.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A system for treatment of constipation in a subject, the system comprising:
   a programmable vibrating ingestible capsule configured to be programmed and activated to implement a vibration protocol defined in a treatment protocol, and configured, in an operative mode, to deliver vibrations to a wall of a gastrointestinal (GI) tract of the subject in accordance with said vibration protocol, thereby to treat the subject;
   a database including data relating to (a) subjects previously treated for disorders in the gastrointestinal tract, (b) treatment protocols used for said subjects, or (c) a response of at least one of said subjects to treatment with a specific treatment protocol used for said at least one of said subjects;
   a capsule control unit including:
      at least one input module configured to receive input from at least one of (i) the subject, (ii) a medical practitioner treating the subject, and (iii) a care giver of the subject;
      a computer readable memory storing a subject profile for the subject, said subject profile including subject data, at least part of said subject data being received, as part of said input, by said at least one input module;
      a communication module for remotely transmitting information to said programmable vibrating ingestible capsule, said information including said vibration protocol; and
      a processor, functionally associated with said at least one input module, said communication module, said computer readable memory, and said database,
   wherein said at least one input module is configured to receive feedback regarding a response of the subject to treatment in accordance with said treatment protocol, and
   wherein said processor is configured to:
      (a) obtain an initial recommendation for an initial recommended treatment protocol based on at least one characteristic included in said subject data;
      (b) generate said treatment protocol based on said initial recommended treatment protocol; and (c) following receipt of said feedback, automatically obtain an updated recommendation for an updated recommended treatment protocol for treating the subject for constipation, said updated recommended treatment protocol to be used in a second programmable vibrating ingestible capsule, said updated recommended treatment protocol being based on said feedback.

2. The system of claim 1, wherein said processor is further configured to:
provide said updated recommended treatment protocol to a decision maker;
receive from said decision maker an indication whether or not another treatment protocol should be identical to said updated recommended treatment protocol; and
when said indication indicates that modifications are required to said updated recommended treatment protocol;
modify said updated recommended treatment protocol in accordance with said modifications to generate said another treatment protocol; and
cause said communication module to remotely transmit said another treatment protocol to said second programmable vibrating ingestible capsule for programming thereof.

3. The system of claim 1, further comprising said second programmable vibrating ingestible capsule configured to be programmed and activated to implement another vibration protocol defined in another treatment protocol, and configured, in an operative mode, to deliver vibrations to said wall of the GI tract of the subject in accordance with said another vibration protocol, thereby to treat the subject, and wherein said capsule control unit is configured to receive from said processor said another vibration protocol and to effect programming of said second programmable vibrating ingestible capsule to implement said another vibration protocol, said another vibration protocol being based on said updated recommended treatment protocol.

4. The system of claim 1, wherein said feedback comprises at least one of:
feedback received from the subject indicating times at which the subject experienced bowel movements during or following said treatment in accordance with said treatment protocol;
feedback received from the subject indicating a physical feeling experienced by the subject during or following said treatment in accordance with said treatment protocol; and
feedback received from the subject indicating at least one characteristic of fecal matter excreted by the subject during or following said treatment in accordance with said treatment protocol.

5. The system of claim 1, further comprising at least one toilet bowl mounted sensor configured to provide to said processor information regarding expelling of said programmable vibrating ingestible capsule from the body of the subject, said information regarding expelling including at least one of:
a time at which said programmable vibrating ingestible capsule was expelled from the body of the subject;
an identification of said programmable vibrating ingestible capsule; and
information regarding at least one characteristic of excrement excreted from the body of the subject.

6. The system of claim 1, wherein said processor is further configured to use said subject data and said received feedback to update said database to reflect said response of the subject to said treatment in accordance with said treatment protocol.

7. The system of claim 1, wherein said updated recommended treatment protocol is distinct from said treatment protocol in at least one of:
a vibration frequency,
a segment in the GI tract in which an operative mode of said second programmable vibrating ingestible capsule should occur,
a length of vibration time within each vibration cycle,
a rest time of each said vibration cycle,
a time of day at which said second programmable vibrating ingestible capsule should be ingested, and
a frequency of treatment using programmable vibrating ingestible capsules.

8. The system of claim 1, wherein said at least one input module is configured to receive said feedback following completion of said treatment of the subject with said programmable vibrating ingestible capsule.

9. The system of claim 1, wherein said updated recommended treatment protocol is further based on said data included in said database, said data relating to at least one other subject of said subjects.

10. The system of claim 1, wherein said updated recommended treatment protocol is further based on said subject data included in said subject profile.

11. A method for treatment of constipation of a subject, the method comprising:
(a) receiving from the subject initial input including subject data and storing the subject data in a subject profile relating to the subject;
(b) obtaining an initial recommendation for an initial recommended treatment protocol based on at least one characteristic included in said subject data;
(c) generating a treatment protocol based on said initial recommended treatment protocol;
(d) using a capsule control unit, programming a programmable vibrating ingestible capsule to implement a vibration protocol defined in said treatment protocol for treatment of constipation;
(e) prior to the subject ingesting said programmable vibrating ingestible capsule, activating said programmable vibrating ingestible capsule to carry out said vibration protocol, said vibration protocol including delivering vibrations to a wall of a GI tract of the subject following ingestion by the subject of the programmable vibrating ingestible capsule, thereby to treat the subject;
(f) receiving feedback regarding a response of the subject to treatment in accordance with said treatment protocol; and
(g) following said treatment of the subject with said programmable vibrating ingestible capsule, automatically and electronically obtaining, at said capsule control unit, an updated recommendation for an updated recommended treatment protocol based on said feedback, wherein said updated recommended treatment protocol is to be used when treating the subject for constipation with a second programmable vibrating ingestible capsule.

12. The method of claim 11, further comprising, following (g):
(h) programming said second programmable vibrating ingestible capsule to implement another vibration protocol defined in another treatment protocol, said another treatment protocol being based on said updated recommended treatment protocol; and (i) prior to the subject ingesting said second programmable vibrating ingestible capsule, activating said second programmable vibrating ingestible capsule to carry out said another vibration protocol, said another vibration protocol including delivering vibrations to said wall of the GI tract of the subject following ingestion by the subject of said second programmable vibrating ingestible capsule, thereby to treat the subject in accordance with said another treatment protocol.

13. The method of claim 12, further including, following (g) and prior to (h):

providing said updated recommended treatment protocol to a decision maker;

receiving from said decision maker an indication whether or not said another treatment protocol should be identical to said updated recommended treatment protocol;

when said indication obtained from said decision maker indicates that said another treatment protocol should be identical to said updated recommended treatment protocol, using said updated recommended treatment protocol as said another treatment protocol; and when said indication obtained from said decision maker indicates that said another treatment protocol should not be identical to said updated recommended treatment protocol:

obtaining from said decision maker at least one change to be made to said updated recommended treatment protocol; and applying said at least one change to said updated recommended treatment protocol, thereby to obtain said another treatment protocol.

14. The method of claim 12, wherein said programming said second programmable vibrating ingestible capsule takes place following said treatment using said programmable vibrating ingestible capsule, and includes:

providing said another vibration protocol to said capsule control unit; and said capsule control unit programming said second programmable vibrating ingestible capsule to implement said another vibration protocol.

15. The method of claim 11, wherein said receiving feedback includes receiving from the subject at least one of:

feedback indicating times at which the subject experienced bowel movements during or following said treatment in accordance with said treatment protocol;

feedback indicating a physical feeling experienced by the subject during or following said treatment in accordance with said treatment protocol; and feedback indicating at least one characteristic of fecal matter excreted by the subject during or following said treatment in accordance with said treatment protocol.

16. The method of claim 11, wherein said receiving feedback includes receiving, from at least one sensor, information regarding expelling of said programmable vibrating ingestible capsule from the body of the subject, said information regarding expelling includes at least one of:

a time at which said programmable vibrating ingestible capsule was expelled from the body of the subject;

an identification of said programmable vibrating ingestible capsule; and information regarding at least one characteristic of fecal matter excreted from the body of the subject.

17. The method of claim 11, further including, following (f), using said feedback together with subject data received from the subject to update said database to reflect said response of the subject to said treatment in accordance with said treatment protocol.

18. The method of claim 11, wherein said updated recommended treatment protocol is distinct from said treatment protocol in at least one of:

a vibration frequency, a segment in the GI tract in which an operative mode of said second programmable vibrating ingestible capsule should occur, a length of vibration time within each vibration cycle, a rest time of each said vibration cycle, a time of day at which said second programmable vibrating ingestible capsule should be ingested, and a frequency of treatment using programmable vibrating ingestible capsules.

19. The method of claim 11, wherein said receiving said feedback comprises receiving said feedback following completion of said treatment of the subject with said programmable vibrating ingestible capsule.

20. The method of claim 11, wherein said updated recommendation for an updated recommended treatment protocol is further based on data included in a database, said data included in said database relating to a response of at least one other subject to treatment using a specific treatment protocol.

21. The method of claim 11, wherein said updated recommendation for said updated recommended treatment protocol is further based on subject data stored in a subject profile relating to the subject.

* * * * *